(12) United States Patent
Rundo et al.

(10) Patent No.: US 11,229,404 B2
(45) Date of Patent: Jan. 25, 2022

(54) PROCESSING OF ELECTROPHYSIOLOGICAL SIGNALS

(71) Applicant: STMicroelectronics S.r.l., Agrate Brianza (IT)

(72) Inventors: Francesco Rundo, Gravina di Catania (IT); Sabrina Conoci, Tremestieri Etneo (IT); Piero Fallica, Catania (IT); Rosalba Parenti, Catania (IT); Vincenzo Perciavalle, Catania (IT)

(73) Assignee: STMICROELECTRONICS S.R.L., Agrate Brianza (IT)

( * ) Notice: Subject to any disclaimer, the term of this patent is extended or adjusted under 35 U.S.C. 154(b) by 436 days.

(21) Appl. No.: 16/195,114

(22) Filed: Nov. 19, 2018

(65) Prior Publication Data
US 2019/0159735 A1   May 30, 2019

(30) Foreign Application Priority Data

Nov. 28, 2017  (IT) ......................... 102017000136598
May 18, 2018  (IT) ......................... 102018000005512

(51) Int. Cl.
*A61B 5/00* (2006.01)
*A61B 5/021* (2006.01)
(Continued)

(52) U.S. Cl.
CPC ............ *A61B 5/7264* (2013.01); *A61B 5/021* (2013.01); *A61B 5/0261* (2013.01);
(Continued)

(58) Field of Classification Search
CPC .... B60W 2540/221; B60W 2040/0872; G06N 20/00; G06N 3/08; G06N 3/0454;
(Continued)

(56) References Cited

U.S. PATENT DOCUMENTS

| 9,019,666 B2 | 4/2015 | Bourgeat et al. |
| 2014/0066785 A1 | 3/2014 | Watson et al. |

(Continued)

FOREIGN PATENT DOCUMENTS

| WO | 2011089179 A1 | 7/2011 |
| WO | 2017089921 A1 | 6/2017 |

OTHER PUBLICATIONS

J. Vicente, P. Laguna, A. Bartra and R. Bailón, "Detection of driver's drowsiness by means of HRV analysis," 2011 Computing in Cardiology, Hangzhou, China, 2011, pp. 89-92. (Year: 2011).*

(Continued)

*Primary Examiner* — Sean P Dougherty
*Assistant Examiner* — Kyle W. Kretzer
(74) *Attorney, Agent, or Firm* — Slater Matsil, LLP

(57) ABSTRACT

Blood pressure signals are reconstructed from PhotoPlethysmoGraphy (PPG) signals by: receiving PPG signals including systolic, diastolic and dicrotic phases; and determining first and second derivatives of the PPG signals and: a first set of values indicative of lengths of the signal paths of the PPG signal, the first derivative and the second derivative thereof in the systolic, diastolic and dicrotic phases; a second set of values indicative of relative durations of the PPG signal and the first and second derivatives thereof in the systolic, diastolic and dicrotic phases; and a third set of values indicative of the time separation of peaks and/or valleys in subsequent waveforms of the PPG signal. Reconstruction also includes applying artificial neural network processing to the first, second and third set of values. The artificial neural network processing includes artificial neural network training as a function of blood pressure signals to produce reconstructed blood pressure signals.

20 Claims, 9 Drawing Sheets

(51) Int. Cl.
| | |
|---|---|
| A61B 5/026 | (2006.01) |
| A61B 5/18 | (2006.01) |
| A61B 5/16 | (2006.01) |
| G06N 3/08 | (2006.01) |
| A61B 5/024 | (2006.01) |
| G16H 10/40 | (2018.01) |

(52) U.S. Cl.
CPC .......... *A61B 5/02108* (2013.01); *A61B 5/168* (2013.01); *A61B 5/18* (2013.01); *A61B 5/6826* (2013.01); *A61B 5/6893* (2013.01); *A61B 5/725* (2013.01); *A61B 5/7239* (2013.01); *A61B 5/7246* (2013.01); *A61B 5/7267* (2013.01); *A61B 5/7278* (2013.01); *G06N 3/08* (2013.01); *A61B 5/02416* (2013.01); *A61B 5/7242* (2013.01); *A61B 2503/22* (2013.01); *G16H 10/40* (2018.01)

(58) Field of Classification Search
CPC ............ G06N 3/02; G05B 2219/39311; A61B 5/7264; A61B 5/0261; A61B 5/7267; A61B 5/6826; A61B 5/02108; A61B 5/7246; A61B 5/725; A61B 5/7278; A61B 5/7242; A61B 5/369; A61B 5/18; A61B 5/168; A61B 5/6893; A61B 2503/22

See application file for complete search history.

(56) References Cited

U.S. PATENT DOCUMENTS

| | | | |
|---|---|---|---|
| 2015/0032382 A1* | 1/2015 | Lee | A61B 5/18 702/19 |
| 2015/0366518 A1 | 12/2015 | Sampson | |
| 2016/0071393 A1 | 3/2016 | Kaplan et al. | |
| 2016/0345907 A1 | 12/2016 | Fung et al. | |
| 2016/0354027 A1 | 12/2016 | Benson et al. | |
| 2017/0172510 A1 | 6/2017 | Homyk et al. | |
| 2018/0192900 A1 | 7/2018 | Wei | |

OTHER PUBLICATIONS

Li, G.; Chung, W.-Y. Detection of Driver Drowsiness Using Wavelet Analysis of Heart Rate Variability and a Support Vector Machine Classifier. Sensors 2013, 13, 16494-16511. https://doi.org/10.3390/s131216494 (Year: 2013).*

Rundo, F., et al., "An innovative Reaction-Diffusion Bio-inspired Pipeline for Physiological Signals Analysis," Proceedings of Italian National Conference on the Physics of Matter, Trieste (Italy), Oct. 1-6, 2017, 2 pages.

Saravanamoorthi, A., et al., "Prediction of Drowsy Fault Using Bio Signals Joint Stachostic FSD (BJSFSD) Algorithm," European Journal of Applied Sciences, 8(4): 193-199, Aug. 2014, 7 pages.

Sari, Nila Novita et al., "A Two-Stage Intelligent Model to Extract Features from PPG for Drowsiness Detection," IEEE International Conference on System Science and Engineering (ICSSE), Jul. 7-9, 2016, pp. 1-2.

Selvaraj, N., et al., "Assessment of heart rate variability derived from finger-tip photoplethysmography as compared to electrocardiography," Journal of Medical Engineering & Technology, Dec. 10, 2008, pp. 479-484.

Shin, Kun-Soo, et al., "An Algorithm for Pattern Recognition of Multichannel ECG Signals," Dept. of Electrical Engineering, Yonsei University, Seoul, Korea, Annual International Conference of the IEEE Engineering in Medicine and Biology Society, vol. 12, No. 2, Nov. 1-4, 1990, 2 pages.

Shin, Hangsik et al., "Feasbility study for the non-invasive blood pressure estimation based on ppg morphology: normotensive subject study," Biomedical Engineering Online, Jan. 10, 2017, pp. 1-14.

Shin, Heung-Sub et al., "Real Time Car Driver's Condition Monitoring System," Sensors, IEEE, Nov. 1, 2010, pp. 951-954.

Shorten, G.P., et al., "A Time Domain Based Classifier for ECG Pattern Recognition," 33rd Annual International Conference of the IEEE Engineering in Medicine and Biology Society, Boston, Massachusetts, Aug. 30-Sep. 3, 2011, pp. 4980-4983.

Soltane, Mohamed et al., "Artificial neural networks (ANN) Approach to PPG Signal Classification," International Journal of Computing & Information Sciences, Apr. 2004, vol. 2(1), pp. 58-65.

Takagi, Tomohiro et al., "Fuzzy Identification of Systems and Its Applications to Modeling and Control," IEEE Transactions on Systems, Man, and Cybernetics, vol. SMC-15, No. 1, Jan. / Feb. 1985, pp. 116-132.

Tang, S.K. Deric et al., "PPG Signal Reconstruction using a combination of Discrete Wavelet Transform and Empirica Mode Decomposition," Faculty of Engineering, Computing & Science, Swinburne University of Technology Sarawak Campus, Malaysia, Aug. 15-17, 2016, 4 pages.

Teng, X. F., et al., "Continuous and Noninvasive Estimation of Arterial Blood Pressure Using a Photoplethysmographic Approach," Proceedings of the 25th Annual International Conference of the IEEE EMBS, Cancun, Mexico, Sep. 17-21, 2003, 4 pages.

Trahanias, Panagiotis et al., "Syntactic Pattern Recognition of the ECG," IEEE Transactions on Pattern Analysis and Machine Intelligence, vol. 12, No. 7, Jul. 1990, pp. 648-657.

Tuzcu, Volkan et al., "Dynamic Time Warping as a Novel Tool in Pattern Recognition of ECG Changes in Heart Rhythm Disturbances," IEEE International Conference on Systems, Man and Cybernetics, Oct. 12, 2005, pp. 182-186.

Vicente, Jose et al., "Detection of Driver's Drowsiness by Means of HRV Analysis," IEEE Computing in Cardiology, Sep. 18-21, 2011, 38, pp. 89-92.

Vinciquerra, Vincenzo et al., "Progresses towards a Processing Pipeline in Photoplethysmogram (PPG) based on SiPMs," IEEE Proceedings of 23 European Conference on Circuit Theory and Design, Catania (Italy), Sep. 4-6, 2017, 5 pages.

Wu, Chih-Chin et al., "A Wireless Photoplethysmography Signal Processing System for Long-term Monitoring," IEEE International Conference on Consumer Electronics (ICCE), Mar. 14, 2016, 4 pages.

Yadhuraj, S. R., et al., "GUI Creation for Removal of Motion Artifact in PPG Signals," 3rd International Conference on Advanced Computing and Communication Systems (ICACCS—2016), Jan. 22-23, 2016, 5 pages.

Yan, Y. S., et al., "Noninvasive Estimation of Blood Pressure Using Photoplethysmographic Signals in the Period Domain," IEEE Engineering in Medicine and Biology 27th Annual Conference, Jan. 17-18, 2006, pp. 3583-3584.

Yeh, Ming-Feng et al., "ECG signal pattern recognition using grey relational analysis," IEEE International Conference on Networking, Sensing and Control, Mar. 21-23, 2004, pp. 725-730.

Yoon, Youngzoon et al., "Nonconstrained Blood Pressure Measurement by Photoplethysmography," Journal of the Optical Society of Korea, vol. 10, No. 2, Jun. 2006, pp. 91-95.

AkayuaChellappa, et al. "Fatigue Detection Techniques: A Review," International Journal of Pure and Applied Mathematics, vol. 117, No. 16, Nov. 16, 2017, 8 pages.

Singh, Rajiv Ranjan, et al. "A comparative evaluation of neural network classifiers for stress level analysis of automotive drivers using physiological signals," Biomedical Signal Processing and Control, vol. 8, No. 6, Nov. 1, 2013, 15 pages.

Abe, Erika et al., "Development of Drowsy Driving Accident Prediction by Heart Rate Variability Analysis", IEEE APSIPA, Dec. 9-12, 2014, 4 pages.

Agro, D., et al., "PPG Embedded System for Blood Pressure Monitoring," IEEE AEIT Annual Conference—From Research to Industry: The Need for a More Effective Technology Transfer (AEIT), Trieste, Sep. 18-19, 2014, 6 pages.

Ali Hassan, M. K., et al., "Measuring Blood Pressure Using a Photoplethysmography Approach," 4th Kuala Lumpur International Conference on Biomedical Engineering, Jan. 2008, 5 pages.

Allen, John "Photoplethysmography and its application in clinical physiological measurement," IOP Publishing, Physiological Measurement, vol. 28, R1-R39, Topical Review, doi: 10.1088/0967-3334/28/3/R01, Mar. 2007, pp. R1-R39.

(56) References Cited

OTHER PUBLICATIONS

Arena, Paolo et al., "A CNN-Based Chip for Robot Locomotion Conlrol," IEEE Transactions on Circuits and Systems—I: Regular Papers, vol. 52, No. 9, Sep. 2005, pp. 1862-1871.

Arena, Paolo et al., "Chaos conlrol by using Motor Maps," Chaos Journal, vol. 12, No. 3, Sep. 2002, pp. 559-573.

Arzi, M., "New Algorithms for Continuous Analysis of Long Term ECG Recordings Using Symplectic Geometry and Fuzzy Pattern Recognition," Computers in Cardiology, Sep. 25-28, 2005, pp. 739-742.

Banerjee, Rohan et al., "Estimation of ECG parameters using photoplethysmography," 13th IEEE International Conference on BioInformatics and BioEngineering, Nov. 10-13, 2013, pp. 1-5.

Barbe, Kurt et al., "Analyzing the Windkessel Model as a Potential Candidate for Correcting Oscillometric Blood-Pressure Measurements," IEEE Transactions on Instrumentation and Measurement, vol. 61, No. 2, Feb. 2012, pp. 411-418.

Battiato, S., et al., "ALZ: Adaptive Learning for Zooming Digital Images," IEEE International Conference on Consumer Electronics, ICCE 2007. Digest of Technical Papers, Jan. 10-14, 2007, 2 pages.

Bolanos, M., et al., "Comparison of Heart Rate Variability Signal Features Derived from Electrocardiography and Photoplethysmography in Healthy Individuals," IEEE Proceedings of the 28th EMBS Annual International Conference, Engineering in Medicine and Biology Society, New York City, Aug. 30-Sep. 3, 2006, pp. 4289-4294.

Cattivelli, Federico S., et al., "Noninvasive Cuffless Estimation of Blood Pressure from Pulse Arrival Time and Heart Rate with Adaptive Calibration," Sixth International Workshop on Wearable and Implantable Body Sensor Networks, Jun. 3-5, 2009, 6 pages.

Datta, Shreyasi et al., "Blood Pressure Estimation from Photoplethysmogram using Latent Parameters," 2016 IEEE International Conference on Communications (ICC), May 22-27, 2016, 7 pages.

Dutt, D. Narayana et al., "Digital Processing of ECG and PPG Signals for Study of Arterial Parameters for Cardiovascular Risk Assessment," IEEE Communications and Signal Processing (ICCSP), Apr. 2-4, 2015, pp. 1506-1510.

Eftestol, Trygve et al., "A Flexible Pattern Recognition System for Analysis of ECG and Related Demographics and Annotations," Proceedings of the 20th Annual International Conference of the IEEE Engineering in Medicine and Biology Society, vol. 20, No. 1, Biomedical Engineering, Nov. 1, 1998, pp. 135-138.

Elgendi, Mohamed "On the Analysis of Fingertip Photoplethysmogram Signals," Current Cardiology Reviews, vol. 8, Feb. 2012, pp. 14-25.

Ferdinando, Hany et al., "Comparing Features from ECG Pattern and HRV Analysis for Emotion Recognition System," IEEE Conference on Computational Intelligence in Bioinformatics and Computational Biology, Oct. 5-7, 2016, 6 pages.

Fletcher, R. et al., "Function minimization by conjugate gradients," The Computing Journal, vol. 7, Issue 2, Jan. 1, 1964 pp. 149-154.

Fortino, Giancarlo et al.,"PPG-based Methods for Non Invasive and Continuous Blood Pressure Measurement: an Overview and Development Issues in Body Sensor Networks," IEEE International Workshop on Medical Measurements and Applications, Apr. 30-May 1, 2010, 4 pages.

Gaurav, Aman et al., "Cuff-Less PPG based Continuous Blood Pressure Monitoring—A Smartphone based Approach," 38th Annual International Conference of the IEEE Engineering in Medicine and Biology Society (EMBC), Aug. 16-20, 2016, 4 pages.

Goldberger, Ary L., et al., "PhysioBank, PhysioToolkit, and PhysioNet Components of a New Research for Complex Physiologic Signals," American Heart Association, Inc., Circulation, Jun. 13, 2000; 101(23): E215-20, 7 pages.

Gu, W. B., et al., "A Novel Parameter from PPG Dicrotic Notch for Estimation of Systolic Blood Pressure Using Pulse Transit Time," Proceedings of the 5th International Workshop on Wearable and Implantable Body Sensor Networks, in conjunction with the 5th International Summer School and Symposium on Medical Devices and Biosensors, Chinese University of Hong Kong, HKSAR, China, Jun. 1-3, 2008, 3 pages.

Hagan, Martin T., et al., "Training Feedforward Networks with the Marquardt Algorithm," IEEE Transactions Neural Network, Nov. 1994; vol. 5, No. 6, pp. 989-993.

He, Lin et al., "Recognition of ECG Patterns Using Artificial Neural Network," Sixth International Conference on Intelligent Systems Design and Applications, Oct. 16-18, 2006, 5 pages.

Huang, Yo-Ping et al., "Early Detection of Driver Drowsiness by WPT and FLFNN Models," IEEE International Conference on Systems, Man, and Cybernetics (SMC), Budapest, Oct. 9-12, 2016, pp. 000463-000468.

Hwang, Taeho et al., "Driver Drowsiness Detection Using the In-Ear EEG," 38th Annual International Conference of the IEEE Engineering in Medicine and Biology Society (EMBC), Orlando, FL., Aug. 16-20, 2016, pp. 4646-4649.

Jeyhani, Vala et al., "Comparison of HRV Parameters Derived from Photoplethysmography and Electrocardiography Signals," Engineering in Medicine and Biology Society (EMBC), 2015 37th Annual International Conference of the IEEE, Aug. 25-29, 2015, pp. 5952-5955.

Jin, Feiming et al., "The Application of Pattern Recognition Technology in the Diagnosis and Analysis on the Heart Disease: Current Status and Future," May 23-25, 2012, 24th Chinese Control and Decision Conference (CCDC), pp. 1304-1307.

Kao, Young-Hua et al., "A PPG Sensor for Continuous Cuffless Blood Pressure Monitoring with Self-Adaptive Signal Processing," Proceedings of the International Conference on Applied System Innovation (ICASI), IEEE-ICASI, 2017—Meen, Prior & Lam (Eds), May 13-17, 2017, 4 pages.

Kavsaoglu, A. Resit et al., "Feature Extraction for Biometric Recognition with Photoplethysmography Signals," IEEE on Signal Processing and Communications Applications Conference (SIU), Apr. 24-26, 2013, 4 pages.

Kim, Jung Yi et al., "Comparative study on artificial neural network with multiple regressions for continuous estimation of blood pressure," Proceedings of the IEEE, Engineering in Medicine and Biology 27th Annual Conference, Shanghai, China, Sep. 1-4, 2005, 4 pages.

Kurylyak, Yuriy et al., "A Neural Network-based Method for Continuous Blood Pressure Estimation from a PPG Signal," IEEE International Instrumentation and Measurement Technology Conference (12MTC), May 6-9, 2013, pp. 280-283.

Kurylyak, Y.,at el., "Smartphone-Based Photoplethysmogram Measurement," in Digital Image, Signal and Data Processing, R.J. Duro and F. López-Peña Ed. Aalborg, Denmark: River Publishers, 2012, pp. 135-164.

Lamonaca, F., et al., "Reliable Pulse Rate Evaluation by Smartphone," IEEE International Symposium on Medical Measurements and Applications Proceedings, May 18-19, 2012, 4 pages.

Lawoyin, Samual, "Novel technologies for the detection and mitigation of drowsy driving," VCU Virginia Commonwealth University, VCU Scholars Compass, Thesis and Dissertations, http://scholarscompass.vcu.edu/etd/3639, Dec. 2014, 320 pages.

Lee, Jaewon et al., "Correlation Analysis between Electrocardiography (ECG) and Photoplethysmogram (PPG) Data for Driver's Drowsiness Detection Using Noise Replacement Method," Procedia Computer Science, vol. 116, Oct. 13-14, 2017, pp. 421-426, ISSN 1877-0509.

Li, Gang et al., "Detection of Driver Drowsiness Using Wavelet Analysis of Heart Rate Variability and a Support Vector Machine Classifier," Sensors (Basel, Switzerland), Dec. 2013(12), www.mdpi.com/journal/sensors, pp. 16494-16511.

Liao, Jia-Ju et al., "An Effective Photoplethysomgraphy Signal Processing System Based on EEMD Method," Department of Electronics Engineering, National Chiao Tung University, Apr. 27-29, 2015, 4 pages.

Liu, Mengyang et al., "Cuffless Blood Pressure Estimation Cased on Photoplethysmography Signal and Its Second Derivative," International Journal of Computer Theory and Engineering, vol. 9, No. 3, Jun. 1, 2017, pp. 202-206.

(56) References Cited

OTHER PUBLICATIONS

Madhav, K. Venu et al., "Estimation of Respilalion Rate from ECG, BP and PPG signals using Empirical Mode Decomposition," IEEE International Instrumentation and Measurement Technology Conference, May 10-12, 2011, pp. 1-4.

Mazomenos, E. B., "A Time-Domain Morphology and Gradient based Algorithm for ECG Feature Extraction," IEEE International Conference on Industrial Technology (ICIT), Mar. 19-21, 2012, pp. 117-122.

Mazzillo, Massimo et al., "Electro-Optical Pof p-on-n and n-on-p Silicon Photomultipliers," IEEE Trans. Electron Devices, vol. 59, No. 12, Dec. 2012, pp. 3419-3425.

Mazzillo, Massimo, et al., "Silicon Photomultiplier Technology at STMicroelectronics," IEEE Transactions on Nuclear Science, vol. 56, No. 4, Aug. 2009, pp. 2434-2442.

McCombie, Devin B., et al., "Adaptive blood pressure estimation from wearable PPG sensors using peripheral artery pulse wave velocity measurements and multi-channel blind identification of local arterial dynamics," Proceedings of the 28th IEEE, EMBS Annual International Conference, New York City, USA, Aug. 30-Sep. 3, 2006, 4 pages.

Meigas, Kalju et al., "Continuous Blood Pressure Monitoring Using Pulse Wave Delay," IEEE Proceedings of the 23rd Annual EMBS International Conference, Oct. 25-28, 2001, Istanbul, Turkey, pp. 3171-3174.

Oreggia, D., et al., "Physiological parameters measurements in a cardiac cycle via a combo PPG-ECG system," Department of Energy, Information Engineering and Mathematical Models (DEIM)—University of Palermo, IMS R&D, STMicroelectronics, Oct. 14-16, 2015, 6 pages.

Page, Adam et al., "Utilizing Deep Neural Nets for an Embedded ECG-based Biometric Authentication System," Oct. 22-24, 2015 IEEE Biomedical Circuits and Systems Conference (BioCAS), pp. 1-4.

Peng, Fulai et al., "Motion artifact removal from photoplethysmographic signals by combining temporally constrained independent component analysis and adaptive filter," BioMedical Engineering OnLine, Apr. 24, 2017, 14 pages.

Raghuram, M., et al., "Use of Complex EMD generated Noise Reference for Adaptive reduction of Motion Artifacts from PPG Signals," Dept. of E&I Eng., Kakatiya Institute of Technology & Science, Dept. of ECE, Talla Padmavathi College of Engineering, Kazipet, International Conference on Electrical, Electronics, and Optimization Techniques (ICEEOT), Mar. 3-5, 2016, 5 pages.

Rundo, Francesco et al., "An Advanced Bio-Inspired PhotoPlethysmoGraphy (PPG) and ECG Pattern Recognition System for Medical Assessment," Sensors, vol. 18, 405, Jan. 2018, 22 pages.

Zhu, Qiang et al., "ECG Reconstruction Via PPG: A Pilot Study," cyclearXiv: 1904.10481v1, Apr. 2019, 4 pages.

\* cited by examiner

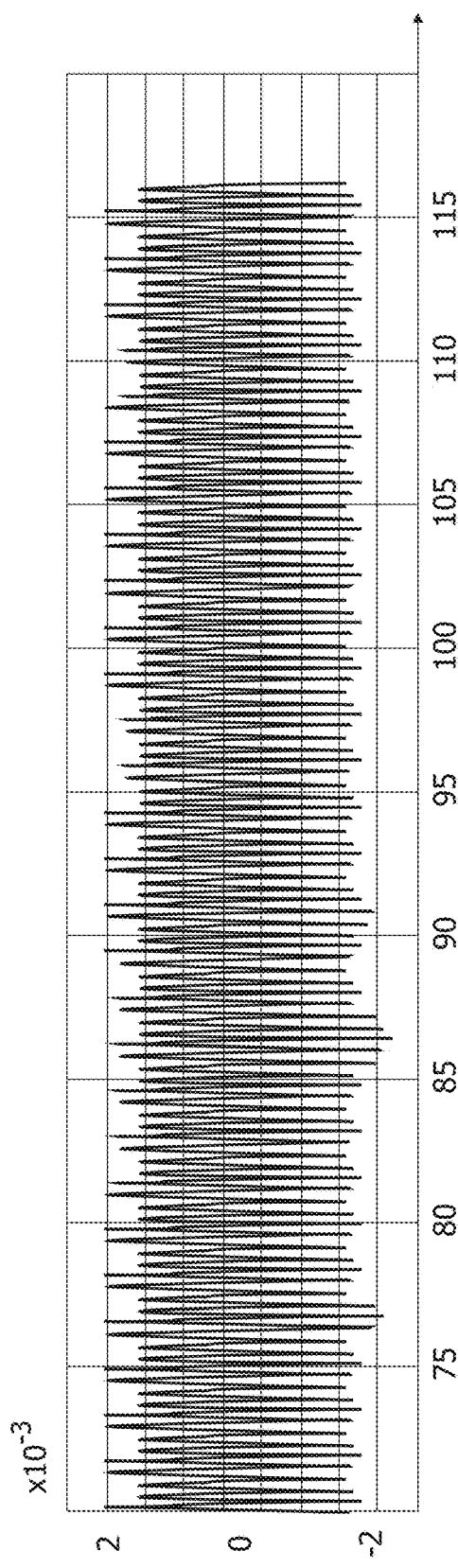
FIG. 3
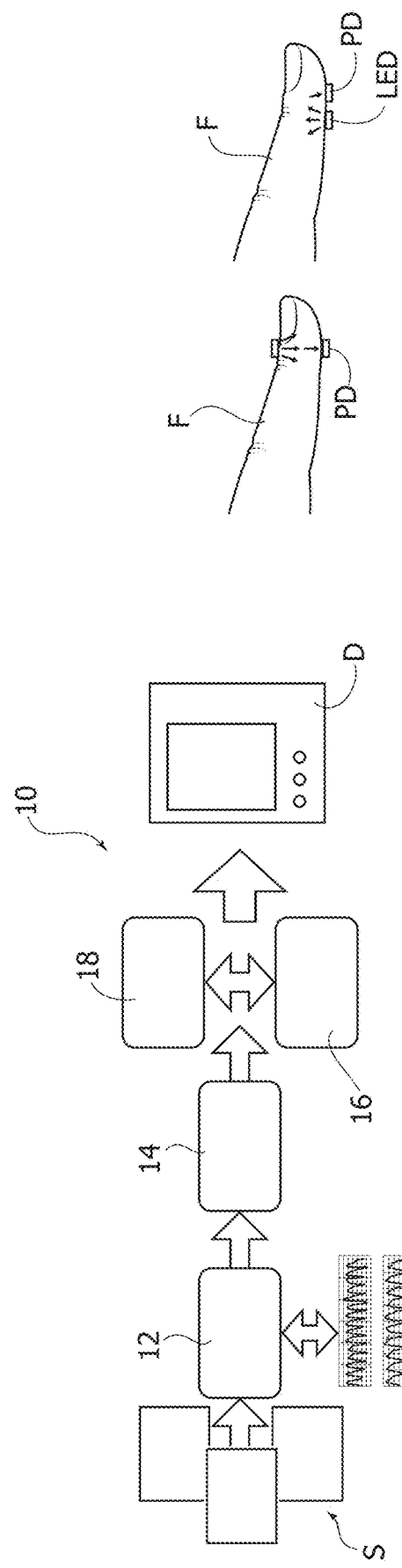
FIG. 6a)  FIG. 6b)
FIG. 5

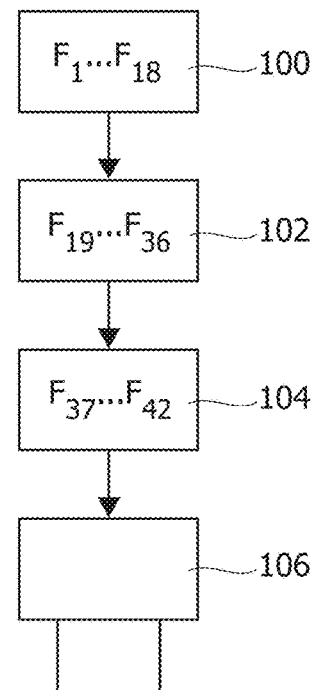
FIG. 7
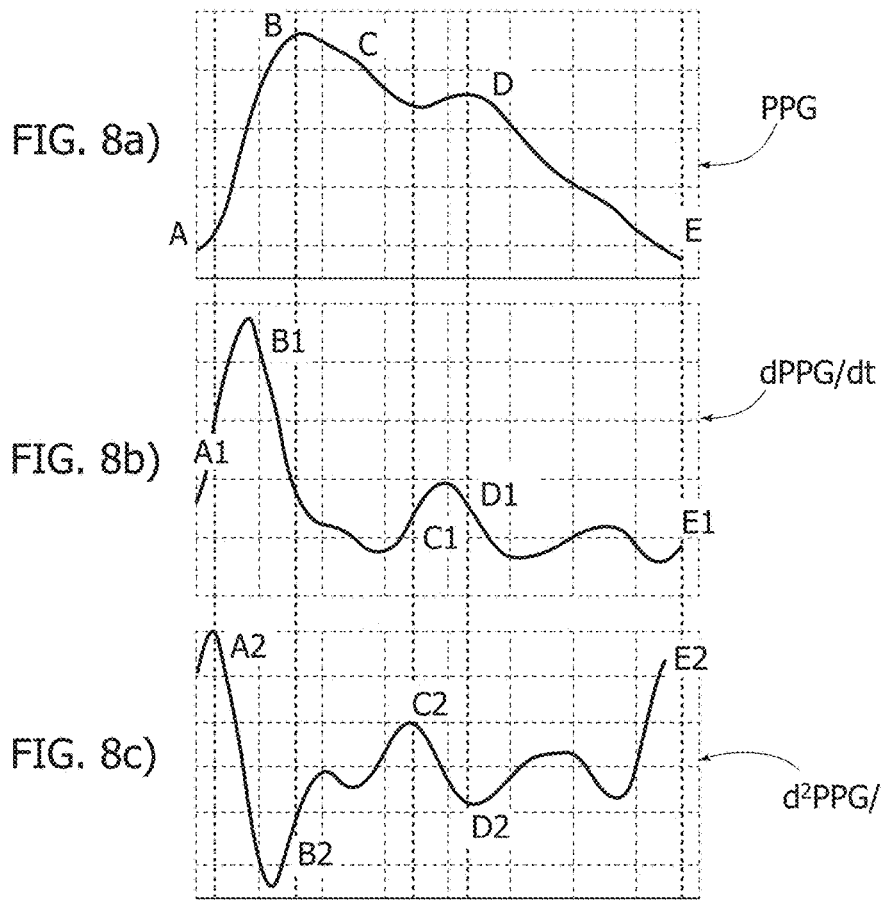
FIG. 8a)
FIG. 8b)
FIG. 8c)

PROCESSING OF ELECTROPHYSIOLOGICAL SIGNALS

CROSS-REFERENCE TO RELATED APPLICATIONS

This application claims the benefit of Italian Application No. 102017000136598, filed on Nov. 28, 2017, and Italian Application No. 102018000005512, filed on May 18, 2018, which applications are hereby incorporated herein by reference.

TECHNICAL FIELD

The description relates generally to processing electrophysiological signals, and in particular embodiments, to a method of processing electrophysiological signals, corresponding system, vehicle, and computer program product.

BACKGROUND

PhotoPlethysmoGraphy (PPG) is a simple and low-cost optical technique that can be used to detect blood volume changes in the microvascular bed of tissue. It is often used non-invasively to make measurements at the skin surface.

A PPG waveform comprises a pulsatile ('AC') physiological waveform attributed to cardiac synchronous changes in the blood volume with each heartbeat, and is superimposed on a slowly varying ('DC') baseline with various lower frequency components attributed to respiration, thermoregulation, skin tissues etc.

For each cardiac cycle the heart pumps blood to the periphery. Even though this pressure pulse is somewhat damped by the time it reaches the skin, it is enough to distend the arteries and arterioles in the subcutaneous tissue. If a light reflex/transmit detector device is attached over the skin, a pressure pulse can also be seen from the venous plexus, as a small secondary peak. The change in volume caused by the pressure pulse is detected by illuminating the skin with the light from a light-emitting diode (LED) and then measuring the amount of light either transmitted or reflected to a photodiode. Each cardiac cycle appears as a peak.

Because blood flow to the skin can be modulated by multiple other physiological systems, the PPG can also be used to monitor breathing, hypovolemia, circulatory conditions as well as for subjective analysis. Additionally, the shape of the PPG waveform differs from subject to subject, and varies with the location and manner in which the pulse oximeter is attached.

Use of PPG may be envisaged also in areas other than the medical field. For instance, PPG has been considered for use in the automotive field e.g. in order to gain useful information on the behavior and/or the reaction of drivers and passengers in various situations which may occur in a motor vehicle.

In fact, extensive activity exists to address the technical problem of identifying a mental attention state, e.g. a drowsy state of a vehicle driver (both before and during the driving), using PPG signals and/or other electrophysiological signals.

Despite the extensive activity in the area of PPG signal detection and processing, improved solutions facilitating the calculation of blood pressure values (for both diastolic and systolic) from PPG signals are desirable. Furthermore, improved solutions facilitating, for instance, identifying a drowsy state of a vehicle driver are desirable.

SUMMARY

An object of one or more embodiments is to contribute in providing such solutions.

One or more embodiments may relate to a corresponding system. One or more embodiments may relate to a corresponding vehicle, such as, for instance, a motor vehicle equipped with such a system.

One or more embodiments may include a computer program product loadable in the memory of at least one processing circuit (e.g., a computer) and including software code portions for executing the steps of the method when the product is run on at least one processing circuit. As used herein, reference to such a computer program product is understood as being equivalent to reference to a computer-readable medium containing instructions for controlling the processing system in order to co-ordinate implementation of the method according to one or more embodiments. Reference to "at least one computer" is intended to highlight the possibility for one or more embodiments to be implemented in modular and/or distributed form.

One or more embodiments may facilitate ElectroEncephaloGraphy (EEG) signal processing (i.e. EEG samples pattern recognition) applied in a PPG/EEG system including, for example: PPG sensors (e.g. Silicon PhotoMultipliers, abbreviated as SiPM, for PPG sensing); a PPG signals pattern recognition method and/or system; an EEG samples pattern recognition system method and/or system.

One or more embodiments may involve a pipeline configured for processing PPG signals based on the use detectors such as e.g. of SiPM detectors. Such probe sensors may provide advantages in terms of single-photon sensitivity and high internal gain for relatively low reverse bias.

One or more embodiments may adopt (possibly in connection with SiPM detectors) a processing pipeline adapted to correct signal distortion, for instance filtering and normalizing the signal.

One or more embodiments thus facilitate obtaining information (data, physical quantities) from the living human or animal body e.g. in support the diagnostic activity of a human in medical and veterinary activities or for other possible uses. Obtaining information on the behavior and/or the reaction of drivers and passengers in the automotive field is exemplary of one such possible use.

One or more embodiments may involve EEG signals processing which facilitate efficient segmentation of compliant EEG sample waveforms in a combined PPG/EEG system, which in turn facilitate robust drowsiness/alert state monitoring of a vehicle driver.

One or more embodiments may offer one or more of the following advantages: high-speed computation facilitated by pattern recognition mechanisms based on Levenberg-Marquardt (LM) algorithm and Multi-Layer Motor Map neural network, which may be implemented in a dedicated hardware; low complexity of data analysis and low CPU consumption; accuracy and robustness due to correlation between PPG and EEG; continuous monitoring of the attention state of a vehicle driver facilitated; possibility of avoiding training algorithms or self-tuning of system parameters; simple implementation for EEG/PPG signal acquisition, e.g., from detectors on the vehicle steering wheel; high sensitivity/specificity ratio (e.g. 98%/98%) versus low complexity design; and reduction of data buffering requirements.

BRIEF DESCRIPTION OF THE DRAWINGS

One or more embodiments will now be described, by way of example only, with reference to the annexed figures, wherein:

FIGS. 2 and 3 are exemplary of the possible time behavior of PPG signals;

FIGS. 4a to 4d illustrate possible behavior of ElectroEncephaloGraphy (EEG) signals;

FIG. 5 is a block diagram of a signal processing pipeline in embodiments;

FIG. 7 is a flow chart exemplary of possible acts of signal processing in embodiments;

FIGS. 8a to 8c and FIG. 9 are diagrams exemplary of certain possible details of processing of PPG signals in embodiments.

DETAILED DESCRIPTION OF ILLUSTRATIVE EMBODIMENTS

In the ensuing description, one or more specific details are illustrated, aimed at providing an in-depth understanding of examples of embodiments of this description. The embodiments may be obtained without one or more of the specific details, or with other methods, components, materials, etc. In other cases, known structures, materials, or operations are not illustrated or described in detail so that certain aspects of embodiments will not be obscured.

Reference to "an embodiment" or "one embodiment" in the framework of the present description is intended to indicate that a particular configuration, structure, or characteristic described in relation to the embodiment is included in at least one embodiment. Hence, phrases such as "in an embodiment" or "in one embodiment" that may be present in one or more points of the present description do not necessarily refer to one and the same embodiment. Moreover, particular conformations, structures, or characteristics may be combined in any adequate way in one or more embodiments.

The references used herein are provided merely for convenience and hence do not define the extent of protection or the scope of the embodiments.

One or more embodiments may be applied to processing electrophysiological signals such as e.g. ElectroEncephaloGraphy (EEG) and/or PhotoPlethysmoGraphy (PPG) signals.

One or more embodiments may facilitate obtaining information (data, physical quantities) from the living human or animal body e.g. in support the diagnostic activity of a human in medical and veterinary activities or for other possible uses (e.g. in the automotive sector).

Figure 1:
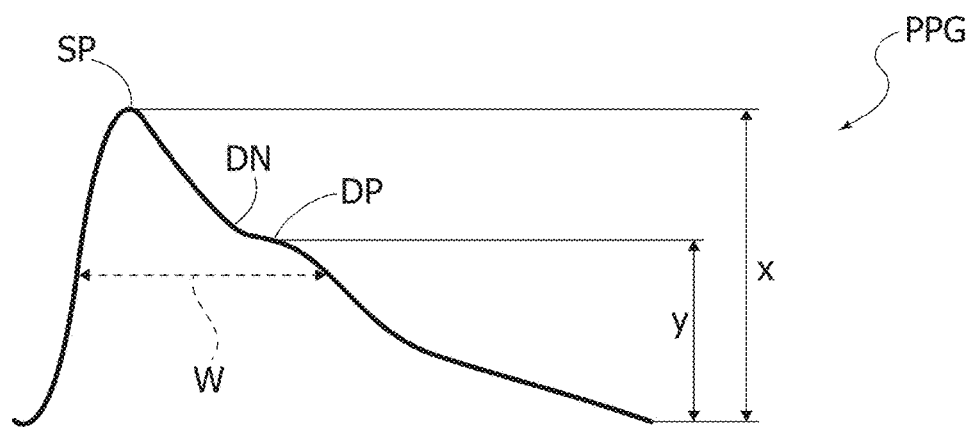
FIG. 1 is a diagram exemplary of a PhotoPlethysmoGraphy (PPG) signal.

As exemplified in FIG. 1, a typical PhotoPlethysmoGraphy (briefly PPG) waveform includes:

a systolic peak SP at a peak value x,
a dicrotic notch DN,
a distolic peak DP at a value y.

A width W of the pulse may also be defined at a given value of the PPG waveform.

Figure 6:
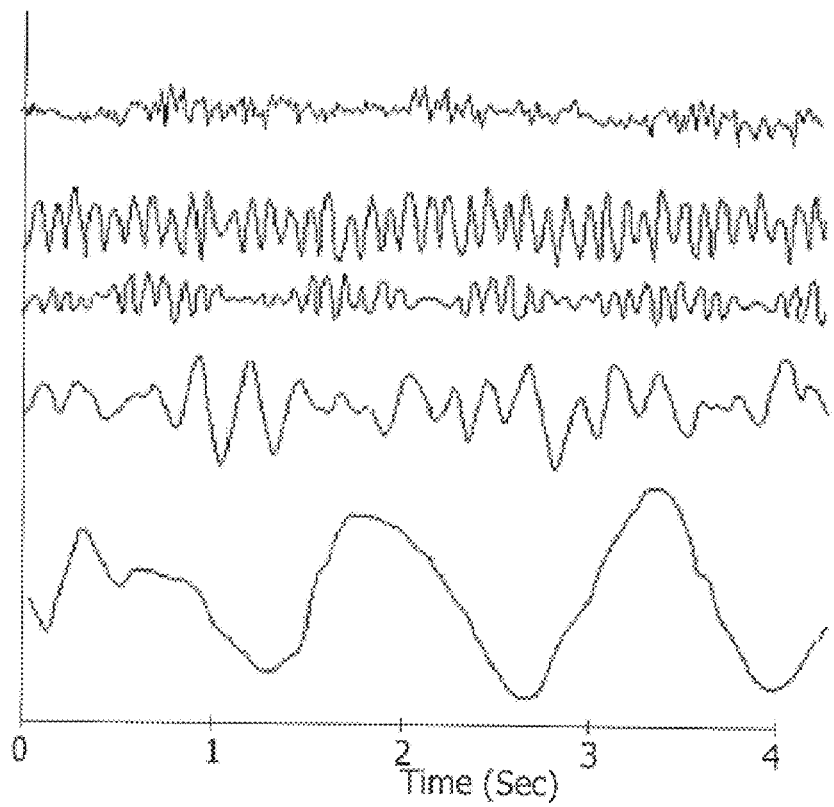
FIGS. 6a and 6b are exemplary of possible operations of PPG sensors.

PPG signals can be detected by using detection devices (e.g. PPG sensors/devices such as sensor PD in FIGS. 6a and 6b) including LED emitters operating at specific wavelengths (usually infrared at 940 nm) and silicon photomultipliers or SiPM's (see e.g. M. Mazzillo, et al.: "Silicon Photomultiplier technology at STMicroelectronics", IEEE Trans. Nucl. Sci, vol. 56, no. 4, pp. 2434–2442, 2009).

As illustrated in FIGS. 6a and 6b, light emitted by the LEDs is absorbed by the skin (DC component) and the arteries, specifically, by oxygenated (and partly by de-oxygenated) hemoglobin (AC component).

Residual propagated/reflected (back-scattered) light will be a function (proportional-differential) of the amount of light absorbed by blood hemoglobin in the various heart phases (systolic, diastolic, dicrotic, etc. . . . ). A SiPM photomultiplier may thus detect the presence of photons in the propagated/reflected light by transducing an electrical signal that can be sampled by an e.g. 24-bit ADC thus providing PPG signal as discussed previously.

Such PPG sensors PD may be applied on a steering device of a vehicle, in various arrangements. One or more embodiments may take advantage of the capability of the PPG sensors PD to operate both in a transmission mode (see FIG. 6a) that is with radiation from the LED propagating through the body (e.g. the body of a patient being clinically investigated or a driver), for instance through a fingertip F, and in a reflection mode (see FIG. 6b) that is with radiation from the LED reflected (back-scattered) from the body, facilitating relaxation of the requirements for possible positioning of the PPG sensors/detectors PD with respect to the body.

An extensive literature exists related to estimating blood pressure, including techniques based on PPG signals.

The following documents are exemplary of activity in that direction:

Y. Kurylyak, et al.: "A Neural Network-based method for continuous blood pressure estimation from a PPG signal", IEEE International Instrumentation and Measurement Technology Conference (I2MTC), 2013 Pages: 280-283;

M. E. Ernst, et al.: "Ambulatory blood pressure monitoring", Southern Medical Journal, vol. 96 (6), pp. 563-568, June 2003;

Y. S. Yan, et al: "Noninvasive estimation of blood pressure using photoplethysmographic signals in the period domain", Proc. of 27th Annual International Conference of the Engineering in Medicine and Biology Society (IEEE-EMBS 2005), 2005, pp. 3583-3584;

K. Barbé, et al: "Analyzing the windkessel model as a potential candidate for correcting oscillometric blood-pressure measurements", IEEE Trans. on Instrum. and Measur., vol. 61, no. 2, pp. 411-418, Feb. 2012;

W. B. Gu, C., et al: "A novel parameter from PPG dicrotic notch for estimation of systolic blood pressure using pulse transit time", Medical Devices and Biosensors (ISSS-MDBS 2008), 2008, pp. 86-88;

K. Meigas, et al: "Continuous blood pressure monitoring using pulse wave delay", Proc. of 23rd Annu. Int. Conf. of the IEEE Eng. in Medicine and Biology Society, vol. 4, 2001, pp. 3171-3174;

M. K. Ali Hassan, et al.: "Measuring blood pressure using a photoplethysmography approach", Proc. of 4th Kuala Lumpur Int. Conf. on Biom. Eng., Vol. 21, 2008, pp. 591-594;

J. Yi Kim, et al.: "Comparative study on artificial neural network with multiple regressions for continuous estimation of blood pressure", Proc. of 27th Annual Intern. Conf. of the Engin. in Medicine and Biology Soc., 2005, pp. 6942-6945;

F. S. Cattivelli, at al.: "Noninvasive cuffless estimation of blood pressure from pulse arrival time and heart rate with adaptive calibration", Proc. of Sixth International Workshop on Wearable and Implantable Body Sensor Networks (BSN 2009), 2009, pp. 114-119;

D. B. McCombie, at al.: "Adaptive blood pressure estimation from wearable PPG sensors using peripheral artery pulse wave velocity measurements and multi-channel blind identification of local arterial dynamics", Proc. of 28th Annual International Conference of the IEEE Eng. In Medicine and Biology Society (EMBS '06), 2006, pp. 3521-3524;

X. F. Teng, et al: "Continuous and noninvasive estimation of arterial blood pressure using a photoplethysmographic approach", Proc. of 25th Annual Inter. Conf. of the IEEE Engineering in Medicine and Biology Society, Cancun, Mexico, 2003, pp. 3153-3156;

Y. Yoon, at al.: "Nonconstrained blood pressure measurement by photoplethysmography", Journal of the Optical Society of Korea, vol. 10, no. 2, pp. 91-95, June 2006;

G. Fortino, et al.: "PPG-based methods for non invasive and continuous BP measurement: an overview and development issues in body sensor networks", Proc. of IEEE Int. Workshop on Medical Measur. and Applications (MeMeA'2010), Ottawa, ON, 2010, pp. 10-13;

A. L. Goldberger, et al.: "PhysioBank, PhysioToolkit, and PhysioNet: Components of a New Research Resource for Complex Physiologic Signals," Circulation 101 (23), pp. e215-e220, 2000;

Y. Kurylyak, at al.: "Smartphone-Based Photoplethysmogram Measurement", in Digital Image, Signal and Data Processing, R. J. Duro and F. Lopez-Peña Ed. Aalborg, Denmark: River Publishers, 2012, pp. 135-164;

F. Lamonaca, at al.: "Reliable pulse rate evaluation by smartphone", Proc. of IEEE Int. Symp. Medical Measurements and Applications (MeMeA 2012), Budapest, Hungary, 2012, pp. 234-237;

A. Gaurav, et al.: "Cuff-less PPG based continuous blood pressure monitoring—A smartphone based approach", 2016 38th Annual International Conference of the IEEE Engineering in Medicine and Biology Society (EMBC) Year: 2016;

S. Datta, et al.: "Blood pressure estimation from photoplethysmogram using latent parameters", 2016 IEEE International Conference on Communications (ICC) Year: 2016 Pages: 1-7, DOI: 10.1109/ICC.2016.7511599;

Yung-Hua Kao, et al.: "A PPG sensor for continuous cuffless blood pressure monitoring with self-adaptive signal processing", 2017 International Conference on Applied System Innovation (ICASI) Year: 2017 Pages: 357-360, DOI: 10.1109/ICASI.2017.7988426.

In general terms, solutions as discussed previously may involve one or more of the following: classical analytic methods; PIT (Pulse Transit Time) based methods, involving both ECG (ElectroCardioGraphy) and PPG signals; heuristic approaches based on key features of PPG standard waveforms; (artificial) neural networks/machine learning algorithms; and mixed ECG-PPG approaches.

It was noted that various solutions as discussed previously may suffer from certain limitations, such as:

they require knowledge of specific physical parameters (arterial vessel elasticity—Moens-Korteweg equation, etc.);

the related systems, both hardware (HW) and software (SW) (PPG/ECG sensors, data extraction (pulse transmit time (PTT), pulse wave velocity (PWV), or the like) may turn out to be unduly complex;

a sensitivity/specificity ratio hardly compatible with the related (high) computational costs;

continuous ECG acquisition may be mandatory, with related difficulties of detection in certain contexts such as the automotive sector or smartphone systems;

those methods which are based on machine learning and (artificial) neural networks (ANN's) may involve high computational costs against a reduced accuracy and/or an estimation capability limited to a reduced pressure range (80-90/110-125 mmHg).

Italian patent application No. 102017000120714 (see corresponding U.S. patent application Ser. No. 16/167,817, which application is hereby incorporated herein by reference) discloses a system including PPG sensing circuitry configured for sensing PPG signals indicative of the driver's heart pulsatile activity, as well as (artificial) neural network processing circuitry sensitive to ECG signals and configured for calculating a correlation between the sample ECG signals sensed over a limited time duration and the PPG signals. The ECG signals are reconstructed from the PPG signals sensed as a function of the correlation between the sample ECG signals sensed and the PPG signals. Such a system may be configured for estimating the heart rate variability (HRV) of the heart of the driver of vehicle and produce a corresponding indicator of the driver's drowsiness.

Figure 2:
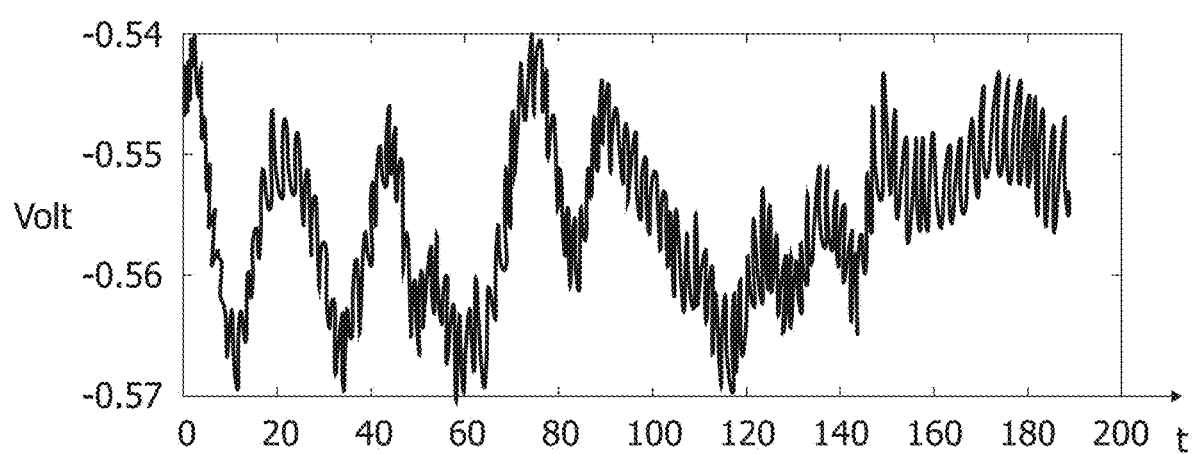

In order to produce from "raw" PPG signals as sensed (see e.g. FIG. 2) "clean" PPG signals which facilitate processing (see e.g. FIG. 3) such a system—and likewise one or more embodiments as exemplified herein—may adopt a solution as described in another Italian Patent Application No. 102017000081018 (see corresponding U.S. patent application Ser. No. 16/037,328, which application is hereby incorporated herein by reference) and also discussed in: F. Rundo et al.: "Progresses towards a Processing Pipeline in Photoplethysmogram (PPG) based on SiPMs", IEEE Proceedings of 23 European Conference on Circuit Theory and Design, Catania (Italy) 4-6 Sep. 2017; F. Rundo et al.: "An innovative Reaction-Diffusion Bio-inspired Pipeline for Physiological Signals Analysis", Proceedings of Italian National Conference on the Physics of Matter, Trieste (Italy), 1-6 Oct. 2017; and F. Rundo et al.: "Innovative pattern recognition algorithm for Photoplethysmography (PPG) measurements", Proceedings of Italian National Conference on the Physics of Matter, Trieste (Italy), 1-6 Oct. 2017.

One or more embodiments as exemplified herein may facilitate determining a correlation between blood pressure and the PPG signal (for a same individual) which is partly linear and partly nonlinear.

EEG is an electro-physiological method to record electrical activity of the brain (electrocortical or EEG activity). Acquisition of EEG signals can be performed as a non-invasive act, for instance by means of certain number of electrodes (e.g., from 16 to 24 electrodes) placed on the cranium by means of a conductive paste, to facilitate a low resistance connection.

Scientific literature demonstrates that EEG activity is due to the synaptic currents generated by the pyramidal cortical neurons, following the signals coming from other cortical areas or from the sensory thalamus.

The sum of the activity of plural pyramidal neurons gives rise to detectable EEG signals. A pyramidal neuron receives various inputs; if such inputs excite a group of adjacent neurons sufficiently simultaneously (synchronization), EEG activity may present wide and slow waves.

FIGS. 4a to 4d are exemplary of EEG signals. As exemplified in FIGS. 4a to 4d, an EEG signal may include waves of different frequency and amplitude, often called "rhythms" and labeled by Greek letters: α, β, δ, θ. The amplitude variation of these waves is specifically related to: physiological events (e.g., sensory stimulation, sleep, etc.) and/or pathological events (e.g., epilepsy, coma, etc.).

In EEG, each "rhythm" may exhibit certain frequency and amplitude characteristics. For instance: the β rhythm (in FIG. 4a) may have a frequency above 13 Hz and amplitude below 40 μV; the α rhythm (in FIG. 4b) may have frequency from 8 to 13 Hz and amplitude from 40 to 50 μV; the θ rhythm (in FIG. 4c) may have frequency from 4 to 7 Hz and amplitude from 50 to 75 μV; the δ rhythm (in FIG. 4d) may have a frequency lower than 4 Hz and amplitude greater than 75 μV. The synchronization of EEG "rhythms" therefore reflects the collective behavior of the neurons involved.

As known from the literature, EEG recordings—for instance the α and β waves—may be (directly) indicative of drowsy and attentive condition of a person, respectively. Other electrophysiological signals, such as, for instance, electrocardiogram (ECG) signals, only represent indirect measurements.

The diagram of FIG. 5 shows an exemplary circuit (pipeline) for a system 10 according to one or more embodiments.

In one or more embodiments such a pipeline may include an input circuit block 12 configured to receive "raw" PPG signals (see e.g. FIG. 2) from a PPG probe section S and produce therefrom "clean" PPG signals (see e.g. FIG. 3).

In one or more embodiments, the pipeline 10 may include a mathematical analysis circuit block 14 (e.g. a processor) which receives the PPG signals from the input circuit block 12 and provides signals corresponding to the results of mathematical analysis (e.g. as exemplified in the following) to first and a second artificial neural network (ANN) circuit blocks 16 and 18, respectively.

The first and second artificial neural network circuit blocks 16 and 18 provide output signals SBP, DBP indicative of the systolic and diastolic blood pressure of the individual whose PPG signals are detected via the PPG probe section S.

The output signals SBP, DBP can be provided to a "consumer" unit D (which per se may be a distinct element from one or more embodiments), which may include e.g. a display screen, a printer, a recording device, etc. so that the signals SBP, DBP may be made available e.g. to support the diagnostic activity of a practitioner in medical and veterinary activities.

In other possible areas of use (e.g. in the automotive sector), the "consumer" unit D may be any circuit adapted to exploit the signals SBP, DBP, e.g. for detecting drowsiness or other possible conditions of a driver or pilot.

The PPG probe section S (which per se may be a distinct element from one or more embodiments) can be based on the use of large area n-on-p SiPMs fabricated at STMicroelectronics (see e.g. M. Mazzillo, et al.: "Silicon Photomultiplier technology at STMicroelectronics", IEEE Trans. Nucl. Sci, vol. 56, no. 4, pp. 2434-2442, 2009, already cited).

These SiPMs may have a total area of 4.0×4.5 mm2 and 4871 square microcells with 60 micron (1 micron=$10^{-6}$ m) pitch. These devices have a geometrical fill factor of 67.4% and are packaged in a surface mount housing (SMD) with 5.1×5.1 mm2 total area (see e.g. M. Mazzillo, et al., cited above or M. Mazzillo, et al.: "Electro-optical performances of p-on-n and n-on-p silicon photomultipliers", IEEE Trans. Electron Devices, vol. 59, no. 12, pp. 3419-3425, 2012).

A Pixelteq dichroic bandpass filter with a pass band centered at 542 nm with a Full Width at Half Maximum (0) of 70 nm (1 nm=$10^{-9}$ m) and an optical transmission higher than 90% in the pass band range can be glued on the SMD package by using a Loctite® 352™ adhesive. With the dichroic filter at 3V-OV the SiPM has a maximum detection efficiency of about 29.4% at 565 nm and a PDE of about 27.4% at 540 nm (central wavelength in the filter pass band −1 nm=$10^{-9}$ m). It was noted that the dichroic filter can reduce in excess of 60% the absorption of environmental light in the linear operation range of the detector operating in Geiger mode above its breakdown voltage (~27V). OSRAM LT M673 LEDs in SMD package emitting at 529 nm (1 nm=$10^{-9}$ m) and based on InGaN technology have been used as optical light sources in exemplary embodiments. These LEDs have an area of 2.3×1.5 mm2, viewing angle of 120°, spectral bandwidth of 33 nm (1 nm=$10^{-9}$ m) and typical power emission of a few mW in the standard operation range.

Use of PPG probes including SiPM detectors may provide advantages in terms of single-photon sensitivity and high internal gain for relatively low reverse bias.

It has been observed that SiPM detectors can provide advantages in PPG systems in terms of higher AC-to-DC ratio in PPG pulse waveform, high repeatability and immunity to motion artifacts and ambient interferences. One or more embodiments as discussed herein may sense PPG signals by using SiPMs (as available with companies of the ST group) as optical probe sensors, adapted to be used in conjunction with hardware and software components in providing a signal processing pipeline.

One or more embodiments may take advantage of the capability of such PPG probes/detectors of operating both in a transmission mode (see FIG. 6a) that is with radiation from the LED propagating through the body (e.g. the body of a patient being clinically investigated or a driver), for instance through a fingertip F, and in a reflection mode (see FIG. 6b) that is with radiation from the LED reflected (back-scattered) from the body.

This permits to further relax the requirements for possible positioning of the PPG probes/detectors with respect to the body.

As noted, in one or more embodiments the input circuit block 12 can be configured to produce "clean" PPG signals (see e.g. FIG. 3) from "raw" PPG signals (see e.g. FIG. 2) as received from the PPG probe section S by adopting the solution described in Italian Patent Application No. 102017000081018 (see corresponding U.S. patent application Ser. No. 16/037,328, and the various Rundo et al. papers already cited in the foregoing.

It will be otherwise appreciated that: while desirable, such "cleaning" of the PPG signals from the PPG probe section S may not be mandatory, so that, at least in certain embodiments, the input circuit block 12 may be dispensed with or at least simplified, e.g. in the form of a filter; and in one or more embodiments, the PPG signals from the PPG probe section S may be "cleaned" by resorting to solutions different from those described in Italian Patent Application No. 102017000081018 (see corresponding U.S. patent application Ser. No. 16/037,328, and the Rundo et al. papers.

In one more embodiments, the mathematical analysis circuit 14 block may include a processor block (e.g. a DSP or similar processor circuit) configured, in a manner known per se (e.g. via software) to perform analysis of the PPG signal from the PPG probe section S (e.g. as received—in digital form—from the input circuit block 12) to extract therefrom certain features to support further processing in the artificial neural network circuits 16 and 18.

As a first act exemplified by the block boo in the flow chart of FIG. 7, the circuit block 14 will calculate a first set of features of the (e.g. filtered) PPG waveform denoted PPG (see e.g. FIG. 8a) and the first and second (time) derivatives thereof ∂PPG/∂t and ∂2PPG/∂t2 (see e.g. FIGS. 8b and 8c).

The following equations F1 to F18 are exemplary of how such first act of processing can be performed in embodiments:

$$F_1 = \ln\left(\frac{1}{N_{PPG}}\left(\sum_{i=1}^{N_{PPG}} L_{sys}^i\right)\right)$$

$$F_2 = \ln\left(\frac{1}{N_{PPG}}\left(\sum_{i=1}^{N_{PPG}} L_{sys}^i\left(\frac{\partial PPG}{\partial t}\right)\right)\right)$$

$$F_3 = \ln\left(\frac{1}{N_{PPG}}\left(\sum_{i=1}^{N_{PPG}} L_{sys}^i\left(\frac{\partial^2 PPG}{\partial t^2}\right)\right)\right)$$

$$F_4 = \sigma_{L_{sys}}$$

$$F_5 = \sigma_{L_{sys}}\left(\frac{\partial PPG}{\partial t}\right)$$

$$F_6 = \sigma_{L_{sys}}\left(\frac{\partial^2 PPG}{\partial t^2}\right)$$

$$F_7 = \ln\left(\frac{1}{N_{PPG}}\left(\sum_{i=1}^{N_{PPG}} L_{dia}^i\right)\right)$$

$$F_8 = \ln\left(\frac{1}{N_{PPG}}\left(\sum_{i=1}^{N_{PPG}} L_{dia}^i\left(\frac{\partial PPG}{\partial t}\right)\right)\right)$$

$$F_9 = \ln\left(\frac{1}{N_{PPG}}\left(\sum_{i=1}^{N_{PPG}} L_{dia}^i\left(\frac{\partial^2 PPG}{\partial t^2}\right)\right)\right)$$

$$F_{10} = \sigma_{L_{dia}}$$

$$F_{11} = \sigma_{L_{dia}}\left(\frac{\partial PPG}{\partial t}\right)$$

$$F_{12} = \sigma_{L_{dia}}\left(\frac{\partial^2 PPG}{\partial t^2}\right)$$

$$F_{13} = \ln\left(\frac{1}{N_{PPG}}\left(\sum_{i=1}^{N_{PPG}} L_{dic}^i\right)\right)$$

$$F_{14} = \ln\left(\frac{1}{N_{PPG}}\left(\sum_{i=1}^{N_{PPG}} L_{dic}^i\left(\frac{\partial PPG}{\partial t}\right)\right)\right)$$

$$F_{15} = \ln\left(\frac{1}{N_{PPG}}\left(\sum_{i=1}^{N_{PPG}} L_{dic}^i\left(\frac{\partial^2 PPG}{\partial t^2}\right)\right)\right)$$

$$F_{16} = \sigma_{L_{dic}}$$

$$F_{17} = \sigma_{L_{dic}}\left(\frac{\partial PPG}{\partial t}\right)$$

$$F_{18} = \sigma_{L_{dic}}\left(\frac{\partial^2 PPG}{\partial t^2}\right)$$

where:
ln denotes (natural) logarithm,
$N_{PPG}$ are the samples $i=1, \ldots, N_{PPG}$ of the PPG signal available over a period of the PPG signal;
the suffixes sys, dia, and die respectively denote the systolic, diastolic, and dicrotic phases of the PPG signal (see e.g. FIG. 1) which may be identified as the portions A-B, A1-B1, A2-B2 (systolic), B-D, B1-D1, B2-D2 (dicrotic), C-E, C1-E1, C2-E2 (diastolic) in the diagrams (PPG, first derivative, second derivative) of FIGS. 8a to 8c.

$L^i$ indicates the length of sub-curve of PPG waveform, for the systolic, diastolic and dicrotic phases sys, dia and die, respectively; in the same way, $L^i(\partial PPG/\partial t)$ represents the length of the sub-curve of the first derivative of the PPG signal, and $L^i(\partial 2PPG/\partial t2)$ represents the length of the sub-curve of the second derivative of the PPG signal, again for sys, dia and dic, respectively. For the first derivative and second derivative of PPG signal, the Simpson rule can be adopted for computing the length of the curve; and G denotes standard deviation for L;

Essentially, equations F1 to F3, F7 to F9 and F12 to F15 provide an indication of the "length" of the signal curve or path of the PPG signal (and the first and second derivatives thereof) in the systolic, diastolic and dicrotic phases (that is, so to say, "how long" each these signals remains in each phase).

By observing FIGS. 8a to 8c it will in fact be noted that, while extending over a same time duration, the PPG signal (see FIG. 8a), the first derivative signal (see FIG. 8b), and the second derivative signal (see FIG. 8c) will have paths of different lengths and provided e.g. by the Simpson rule.

In the same line, equations F4 to F6, F10 to F12 and F16 to F18 provide a refined indication of the average (standard deviation) of the path lengths of the PPG signal and the first and second time derivatives thereof in the systolic, diastolic and dicrotic phases.

As a second act as exemplified by the block 102 in the flow chart of FIG. 7, the circuit block 14 will calculate a second set of features F19 to F36 of the (e.g. filtered) PPG, ∂PPG/∂t and ∂2PPG/∂t2 signals which are indicative of shape factors of these signals, e.g. relative measures of the of the systolic, diastolic and dicrotic phases.

For instance, these relative measures can be regarded as exemplary of how fast/slow the transitions between the systolic, diastolic and dicrotic phases may occur.

The following equations F19 to F36 are exemplary of how such second act of processing can be performed in embodiments:

$$F_{19} = \frac{1}{N_{PPG}} \sum_{i=1}^{N_{PPG}} \frac{L_{sys}^i}{L_{dia}^i}$$

$$F_{20} = \sigma\left(\frac{L_{sys}}{L_{dia}}\right)$$

$$F_{21} = \frac{1}{N_{PPG}} \sum_{i=1}^{N_{PPG}} \frac{L_{sys}^i}{L_{dia}^i}\left(\frac{\partial PPG}{\partial t}\right)$$

$$F_{22} = \sigma\left(\frac{L_{sys}}{L_{dia}}\left(\frac{\partial PPG}{\partial t}\right)\right)$$

-continued $$F_{23} = \frac{1}{N_{PPG}} \sum_{i=1}^{N_{PPG}} \frac{L^i_{sys}}{L^i_{dia}} \left(\frac{\partial^2 PPG}{\partial t^2}\right)$$

$$F_{24} = \sigma\left(\frac{L_{sys}}{L_{dia}}\left(\frac{\partial^2 PPG}{\partial t^2}\right)\right)$$

$$F_{25} = \frac{1}{N_{PPG}} \sum_{i=1}^{N_{PPG}} \frac{L^i_{sys}}{L^i_{dic}}$$

$$F_{26} = \sigma\left(\frac{L_{sys}}{L_{dic}}\right)$$

$$F_{27} = \frac{1}{N_{PPG}} \sum_{i=1}^{N_{PPG}} \frac{L^i_{sys}}{L^i_{dia}}\left(\frac{\partial PPG}{\partial t}\right)$$

$$F_{28} = \sigma\left(\frac{L_{sys}}{L_{dia}}\left(\frac{\partial PPG}{\partial t}\right)\right)$$

$$F_{29} = \frac{1}{N_{PPG}} \sum_{i=1}^{N_{PPG}} \frac{L^i_{sys}}{L^i_{dic}}\left(\frac{\partial^2 PPG}{\partial t^2}\right)$$

$$F_{30} = \sigma\left(\frac{L_{sys}}{L_{dic}}\left(\frac{\partial^2 PPG}{\partial t^2}\right)\right)$$

$$F_{31} = \frac{1}{N_{PPG}} \sum_{i=1}^{N_{PPG}} \frac{L^i_{dia}}{L^i_{dic}}$$

$$F_{32} = \sigma\left(\frac{L_{dia}}{L_{dic}}\right)$$

$$F_{33} = \frac{1}{N_{PPG}} \sum_{i=1}^{N_{PPG}} \frac{L^i_{dic}}{L^i_{dic}}\left(\frac{\partial PPG}{\partial t}\right)$$

$$F_{34} = \sigma\left(\frac{L_{dia}}{L_{dic}}\left(\frac{\partial PPG}{\partial t}\right)\right)$$

$$F_{35} = \frac{1}{N_{PPG}} \sum_{i=1}^{N_{PPG}} \frac{L^i_{dia}}{L^i_{dic}}\left(\frac{\partial^2 PPG}{\partial t^2}\right)$$

$$F_{36} = \sigma\left(\frac{L_{dia}}{L_{dic}}\left(\frac{\partial^2 PPG}{\partial t^2}\right)\right)$$

where the entities indicated have the same meaning already discussed in connection with equations F1 to F18 for the systolic, diastolic and dicrotic phases (sys, dia and dic), respectively.

Figure 9:
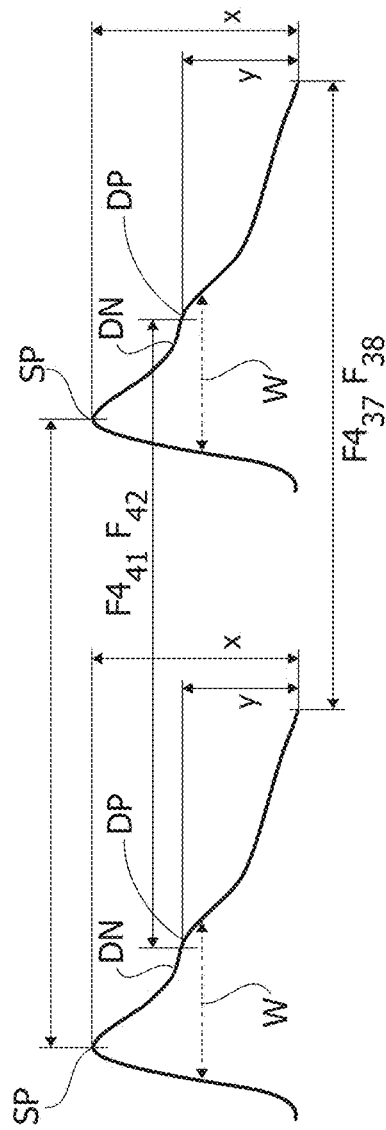

FIG. 9 is exemplary of possible processing which may be performed as exemplified by the block 104 in the flow chart of FIG. 7, where the distances between peaks/valleys in subsequent PPG waveforms (generally denoted i and i+1) are evaluated.

The following equations F37 to F42 are exemplary of how such third act of processing can be performed in embodiments:

$$F_{37} = \ln\left(\frac{1}{N_{PPG}} \sum_{i=1}^{N_{PPG}-1} \left(\min^{i+1}_{dia\text{-}PPG} - \min^{i}_{dia\text{-}PPG}\right)\right)$$

$$F_{38} = \ln\left(\sigma\left(\min^{i+1}_{dia\text{-}PPG} - \min^{i}_{dia\text{-}PPG}\right)\right)$$

$$F_{39} = \ln\left(\frac{1}{N_{PPG}} \sum_{i=1}^{N_{PPG}-1} \left(\max^{i+1}_{sys\text{-}PPG} - \max^{i}_{sys\text{-}PPG}\right)\right)$$

$$F_{40} = \ln\left(\sigma\left(\max^{i+1}_{sys\text{-}PPG} - \max^{i}_{sys\text{-}PPG}\right)\right)$$

$$F_{41} = \ln\left(\frac{1}{N_{PPG}} \sum_{i=1}^{N_{PPG}-1} \left(p^{i+1}_{dic\text{-}PPG} - p^{i}_{dic\text{-}PPG}\right)\right)$$

$$F_{42} = \ln\left(\sigma\left(p^{i+1}_{dic\text{-}PPG} - p^{i}_{dic\text{-}PPG}\right)\right)$$

$$F_{42} = \ln\left(\sigma\left(p^{i+1}_{dic\text{-}PPG} - p^{i}_{dic\text{-}PPG}\right)\right)$$

where the entities already discussed in connection with equations F1 to F36 retain the same meaning and max: denotes the point (abscissa) where the PPG waveform has its maximum value (systolic peak SP);

min: denotes the point (abscissa) where the PPG waveform has its minimum value;

$p^i$ denotes the dicrotic point (abscissa);

i and i+1 generally denote two subsequent PPG waveforms.

The foregoing applies once more for sys, dia and dic, respectively.

FIG. 9 further exemplifies the distances between peaks/valleys as adapted to be expressed by formulas F37-F38, F39-F40 and F41-F42 with reference to subsequent PPG waveforms i and i+1.

The entities (e.g. F1-F42 as exemplified in the foregoing) calculated in circuit block 14 can be input to the artificial neural network (ANN) circuits 16 and 18 to perform therein processing (as exemplified by block 106 in FIG. 6) intended to correlate the PPG signal with pressure measurements (both diastolic and systolic) available for training the neural network circuits 16 and 18 to produce blood pressure signals SBPrec (systolic) and DBPrec (diastolic) reconstructed starting from the PPG signals.

Training values, e.g. SBP(t+1) (systolic) and DBP(t+1) (diastolic) can be derived e.g. from a set of measurements performed on a sample of e.g. 32 patients for which blood pressure is measured (e.g. by conventional means such as a sphygmomanometer) concurrently with detecting a PPG signal. These values can be used for training both neural networks circuits 16 (e.g. Polak-Ribiere neural network multi-layer perceptron) and 18 (e.g. self-organizing map, abbreviated as SOM).

The Polak-Ribiere neural network multi-layer perceptron (as exemplified e.g. in Fletcher R. et al.: "Function minimization by conjugate gradients", Computer Journal, Vol. 7m 1964 pp. 149-154; or Hagan M. T., et al.: "Neural Network Design", Boston, Mass.: PWS Publishing, 1996 pp. 9-15-9-22) was found to be an adequate tool for use in learning a correlation between PPG-based features as discussed previously (e.g. F1-F42) with blood pressure measurements.

The artificial neural network circuit 16 will thus be able to reconstruct the blood pressure of a subject both for systolic (SBP) and diastolic (DBP) values, e.g. in connection with a first, non-linear part or component f1(*)/f2(*)—see below—e.g. based on a Polak-Ribiere neural network multi-layer perceptron.

The artificial neural network circuit 18 will be able to complete such a reconstruction of the blood pressure both for systolic (SBP) and diastolic (DBP) values by detecting a second, linear part or component (K1(*)/K2(*)) for both diastolic and systolic pressures.

In fact, in one or more embodiments, blood pressure values, SBPrec (systolic) and DBPrec (diastolic) were found to be reliably and accurately reconstructed as a combination (e.g. as a sum) of non-linear plus linear components in the form:

SBPrec=f1(Polak-Ribiere NN)+K1(w1[SOM1]); and

DBPrec=f2(Polak-Ribiere NN)+K2(w2[SOM2]), where f1(*) and f2(*) represent the output from a functional mapping modelled by f1(*)-systolic—and f2(*)-diastolic— as produced by the first network 16 (e.g. with Polak-Ribiere learning), which is non-linear function.

The terms K1(*)-systolic—and K2(*)-diastolic—represent the output from the second network 18 (e.g. "Extended SOM"), which is a linear function.

Consequently, the pressure values SBPrec/DBPrec include a non-linear portion (f1/f2) and a linear portion (K1/K2).

Figure 10:
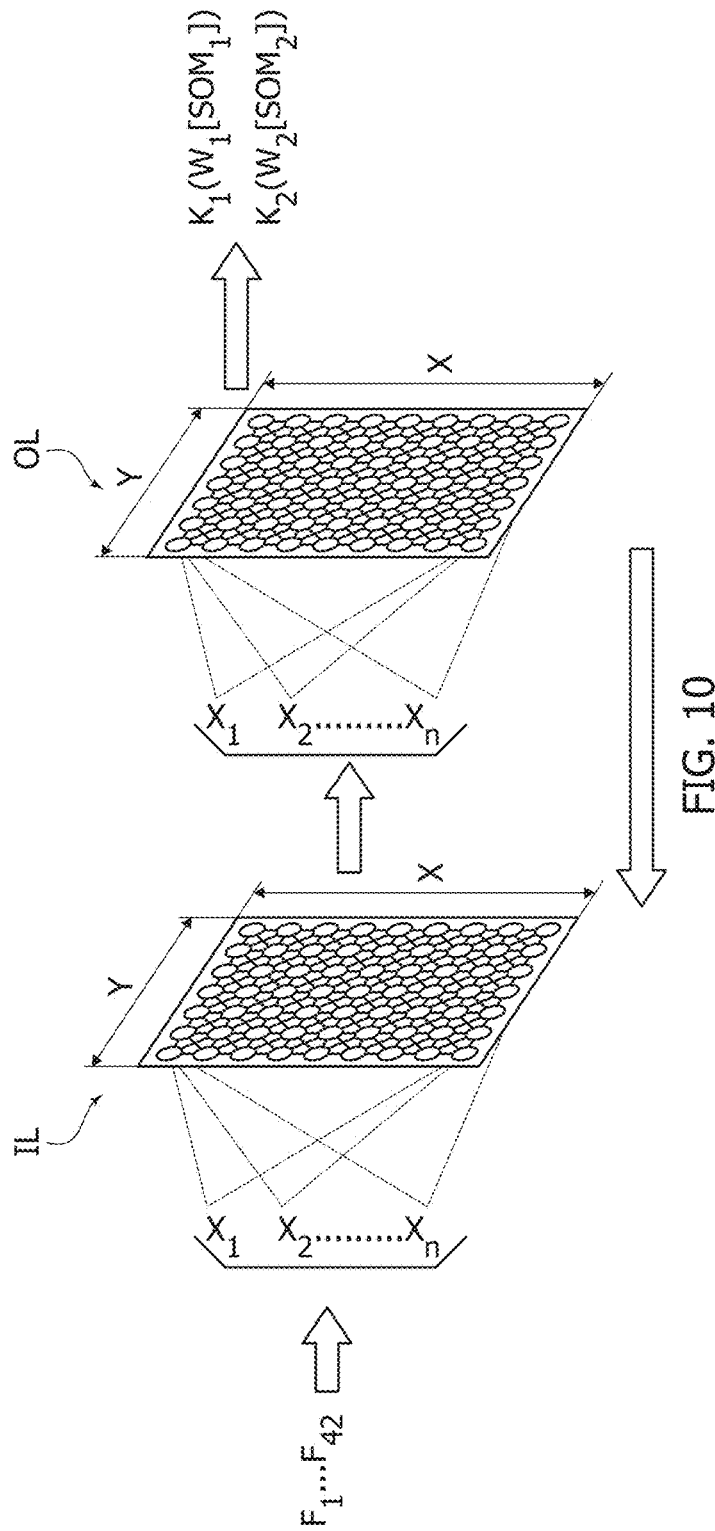
FIG. 10 is a block diagram exemplary of a possible mode of operation of the pipeline of FIG. 5.

An extended SOM as schematically exemplified in FIG. 10 (where only the input layer IL and the output layer OL are visible) was found to be suited for use in one or more embodiments, e.g. due to the presence of an output layer OL where the output weights are used to compute equations such as:

for the systolic blood pressure value SBP:

$$wiin(xmin \cdot ymin \cdot t+1) = wiin(xmin \cdot ymin \cdot t) + \alpha \cdot \beta(x,y,t) \cdot (Fi - wiin(xmin \cdot ymin \cdot t+1))$$

$$K1in(xmin \cdot ymin \cdot t+1) = K1in(xmin \cdot ymin \cdot t) + \alpha \cdot \Sigma \cdot \beta(x,y,t) \cdot ([SBPi - f1(\text{Polak-Ribiere}$$

$$NN)] - K1(xmin \cdot ymin \cdot t+1))$$

$$dw(i,j) = (1/N)\Sigma|Fi - win(i,j,t)|,$$

with an error E(t+1)<E(t) where E(t+1)=[SBP(t+1)−SBPrec(t+1)], where SBPrec denotes the reconstructed systolic blood pressure value; and for the diastolic blood pressure value DBP:

$$wiin(xmin \cdot ymin \cdot t+1) = wiin(xmin \cdot ymin \cdot t) + \alpha \cdot \beta(x,y,t) \cdot (Fi - wiin(xmin \cdot ymin \cdot t+1))$$

$$K2in(xmin \cdot ymin \cdot t+1) = K2n(xmin \cdot ymin \cdot t) + \alpha \cdot \Sigma \cdot \beta(x,y,t) \cdot ([DBPi - f2(\text{Polak-Ribiere}$$

$$NN)] - K2(xmin \cdot ymin \cdot t+1))$$

$$dw(i,j) = (1/N)\Sigma|Fi - win(i,j,t)|,$$

with an error E(t+1)<E(t) where E(t+1)=[DBP(t+1)−DBPrec(t+1)], where DBPrec denotes the reconstructed distolic blood pressure value.

The blood pressure values so computed (both systolic, SBPrec, and diastolic, DBPrec) can thus be supplied to the "consumer" unit D for use as desired (e.g. support of diagnosis by a practitioner or other uses as discussed previously).

A system as exemplified herein was found to be able to provide a blood pressure estimation (both systolic and diastolic) in a few seconds, with (only) 4-5 seconds of PPG sampling found to facilitate accurate and reliable reconstruction of a blood pressure signal.

It will be otherwise appreciated that, while exemplified herein in connection with reconstructing from PPG signals both systolic and diastolic blood pressure values (e.g. SBPrec and DBPrec), certain embodiments may involve the reconstruction only one of those blood pressure values.

As mentioned above, one or more embodiments may involve EEG signals processing which facilitate efficient segmentation of compliant EEG sample waveforms in a combined PPG/EEG system, which in turn facilitate robust drowsiness/alert state monitoring of a vehicle driver. In this regard, reference is made to FIG. 11, which is exemplary of a possible pipeline of signal processing in a system 40 according to embodiments that facilitate robust drowsiness/alert state monitoring of a vehicle driver.

A PPG sensor PD (shown in dashed line, insofar as this may represent a distinct element from embodiments) may be coupled to a first processing circuit block or stage 42 to provide thereto an unprocessed "raw" PPG signal S. In one or more embodiments as discussed herein, the PPG signal may be sensed in a known manner at a location of the body of a driver D of a vehicle V. For instance, the signal may be sensed via one or more PPG sensors (for instance, of the type discussed in the foregoing) arranged at a steering wheel SW of the vehicle V.

One or more embodiments of the processing stage 42 may include filtering stages, mathematical analysis stages and artificial neural network circuits (trained with sample EEG signals/waveforms), whose functions will be discussed in the following, also with reference to figures such as FIGS. 12 to 17.

The output from the processing stage 42 may be coupled to a decision stage 44. In one or more embodiments, the decision stage 44 may include neural networks circuits and/or comparator circuits, as discussed in the following. One or more embodiments of the decision stage 44 may be configured to evaluate a state of the vehicle driver D, for instance by providing a signal DS indicative of the level of attention of the driver D which may be fed to an interface A (for instance a display unit, a sound and/or light generator, and so on). This may facilitate, for instance, making the driver D aware of a reduced level of attention, possibly due to drowsiness or other reasons. In one or more embodiments, the decision stage 44 may also provide signals (e.g., the signal DS) to an error monitoring stage 46.

The error monitoring stage 46 may in turn operate, via a feedback loop path 48, on the processing stage 42 or the decision stage 44 as a function of signals from the decision stage 44 and/or input from the user D (as provided via the interface A, for instance). For instance, the error monitoring stage 46 may trigger the activation of the feedback loop path 48 to facilitate retraining of neural network circuits included in the processing stage 42 and/or in the decision stage 44.

Figure 11:
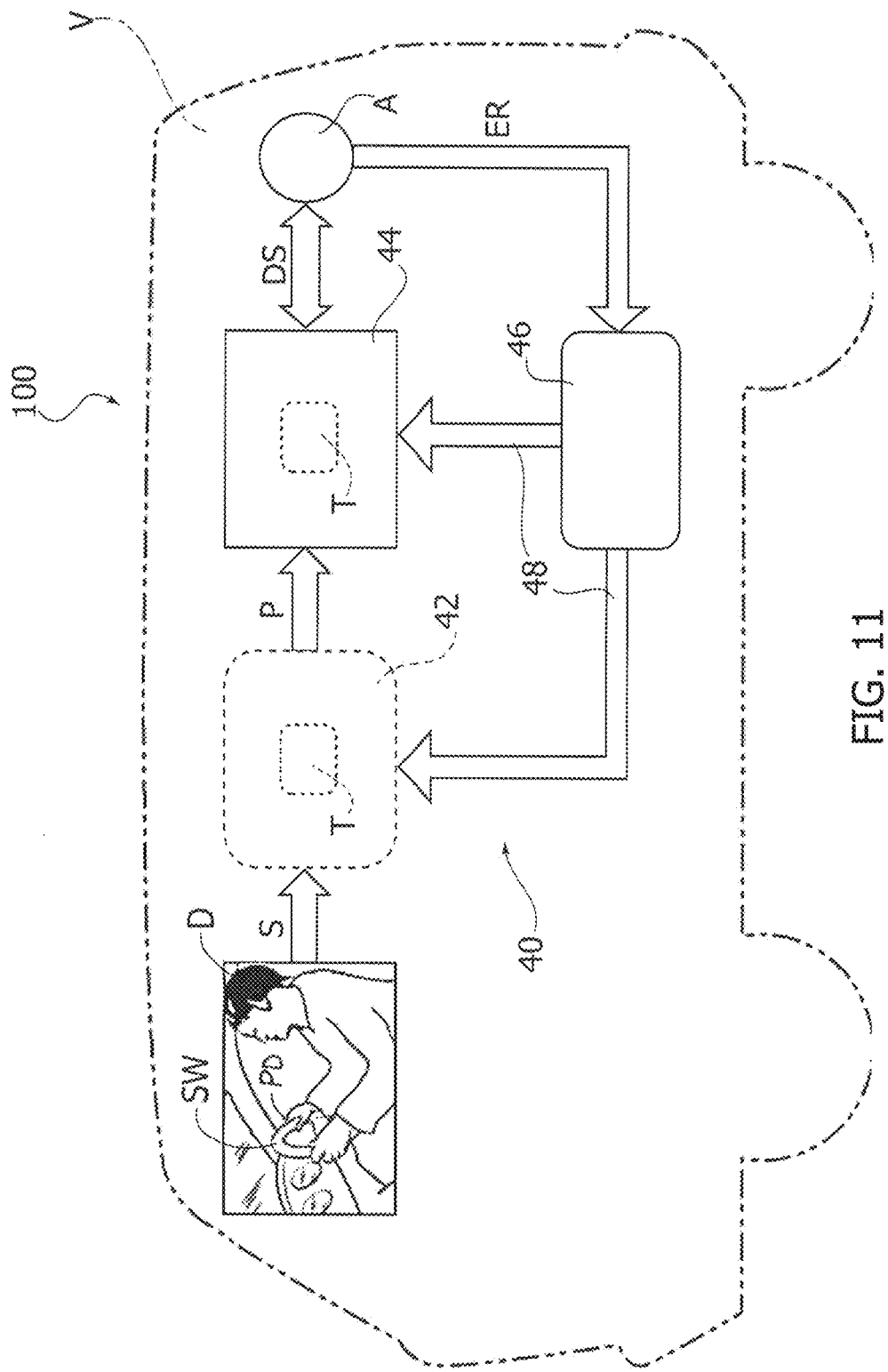
FIG. 11 is a functional diagram exemplary of possible signal processing in embodiments.

As exemplified in FIG. 11, the processing stage 42 may include sub-stages 42a, 42b which may include essentially similar artificial neural network circuits and intended to operate different training datasets e_real_drowsy, e_real_wakeful, as discussed in the following.

Due to the essential similarity of the sub-stages 42a, 42b, for the sake of brevity, in the following a detailed description will be provided primarily in respect to the former one (that is 42a), being otherwise understood that the same description also applies, mutatis mutandis, also to the latter (that is sub-stage 42b). At least in principle, the sub-stages 42a, 42b might even be implemented as a single circuit intended to perform alternatively the role of the sub-stage 42a (dataset e_real_drowsy) and the role of the sub-stage 42b (dataset e_real_wakeful).

Figure 15:
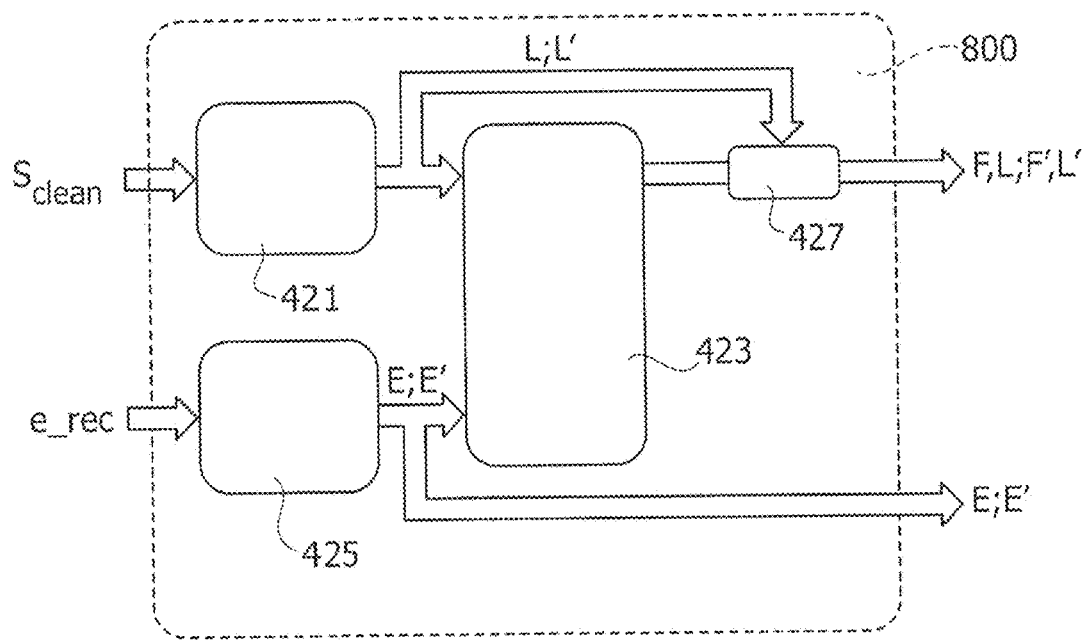
FIG. 15 is a block diagram exemplary of a possible arrangement of a portion of the pipeline of FIG. 11.

In one or more embodiments, the stage 42a may include a first filtering circuit 420, receiving the "raw" PPG signal S from the sensor PD and providing a filtered "clean" PPG signal Sclean to both a normalization stage 422 and a mathematical analysis stage 800 (see FIG. 15).

In order to produce, from a "raw" PPG signal S, sensed by the sensor PD, a "clean" PPG signal Sclean which facilitate processing, the first filtering stage 420 may adopt a solution as described above in respect of Italian Patent Application No. 102017000081018 and the various Rundo et al. papers cited in the foregoing. It will be otherwise appreciated that while desirable, such "cleaning" of the PPG signals from the PPG probe section PD may not be mandatory, so that, at least in certain embodiments, the first filtering stage 420 may be dispensed with or at least simplified, e.g. in the form of a filter.

In one or more embodiments as exemplified herein, the normalization stage 422 may receive a "clean" PPG signal Sclean and provide a normalized PPG signal to a downstream first artificial neural network circuit (briefly, ANN) 424. For instance, the normalization stage 422 may process the "clean" PPG signal Sclean to a unitary range [0,1] prior to segmentation of the PPG signal. The PPG segmented waveform obtained may be further normalized and resized e.g. via a nearest algorithm (see e.g. F. Rundo, et al.: "Adaptive Learning for Zooming Digital Images"—ICCE 2007. Digest of Technical Papers. International Conference on Consumer Electronics, 2007) in order to make it comparable (in terms of value and as regards the time-axis) with other PPG waveforms.

In one or more embodiments, the normalized PPG signal Sclean may be received by the downstream first ANN 424 which may process the signal as to provide a "reconstructed" EEG signal e_rec to downstream second ANN stage 426 and mathematical analysis stage 800.

In one or more embodiments, the first ANN 424 may include a storage area for a collection of sample EEG waveforms e_real. As noted, in one or more embodiments the sub-stages 42a and 42b may be intended to operate different training datasets e_real_drowsy, e_real_wakeful. Consequently, in the sub-stage 42a, the first ANN 424 may store a collection e_real_drowsy of EEG waveforms of drivers in a drowsy state; and in the sub-stage 42b, the first ANN 424 may store a collection e_real_wakeful of EEG waveforms of drivers in a wakeful state.

In one or more embodiments, "reconstructed" EEG signals e_rec may be calculated in the first ANN's 424 of the two stages 42a, 42b as a function of: the PPG signal from the PPG probe PD; and the respective collection of EEG waveforms, namely e_real_drowsy (stage 42a) or e_real_wakeful (stage 42b). This processing will thus result in two reconstructed EEG signals, namely a "drowsy" EEG signal e_rec_drowsy (stage 42a) and a "wakeful" EEG signal e_rec_wakeful (in stage 42a, with the signal e_rec_wakeful not visible in FIG. 12).

In one or more embodiments the two signals e_rec_drowsy and e_rec_wakeful may then be further processed (to some extent, compared) with the aim of evaluating—for instance in the block 44) whether the PPG signal S as (currently) detected via the probe PD is indicative of a "drowsy" state or a "wakeful" state of the driver D. This may occur, for instance as discussed in the following with reference to FIG. 17.

Figure 13:
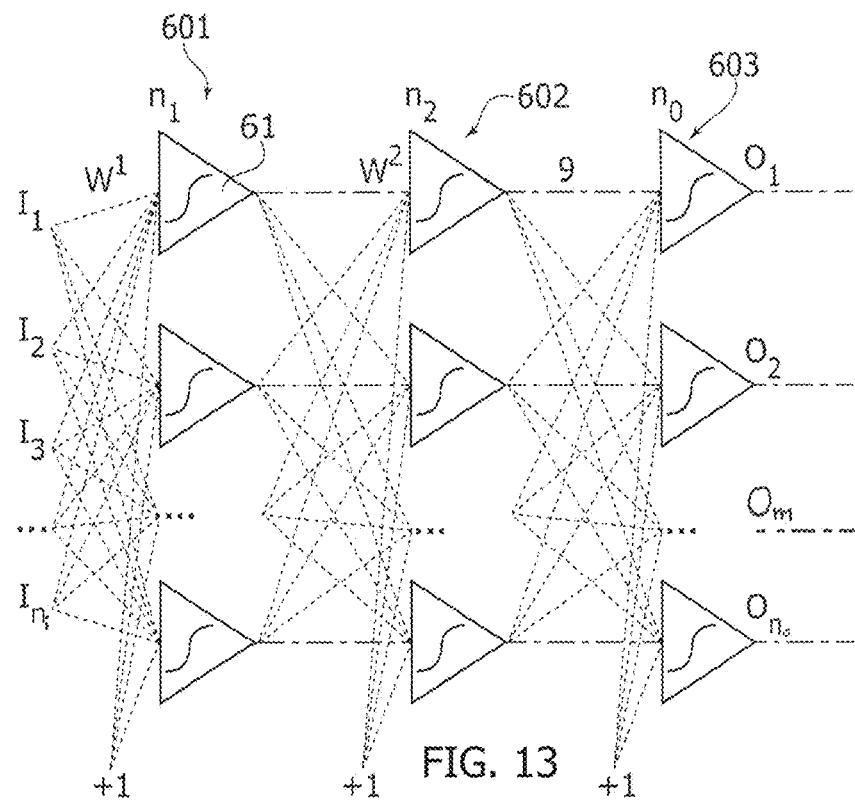
FIGS. 13 and 14 are diagrams exemplary of processing of PPG signals in the pipeline of FIG. 11.
Figure 14:
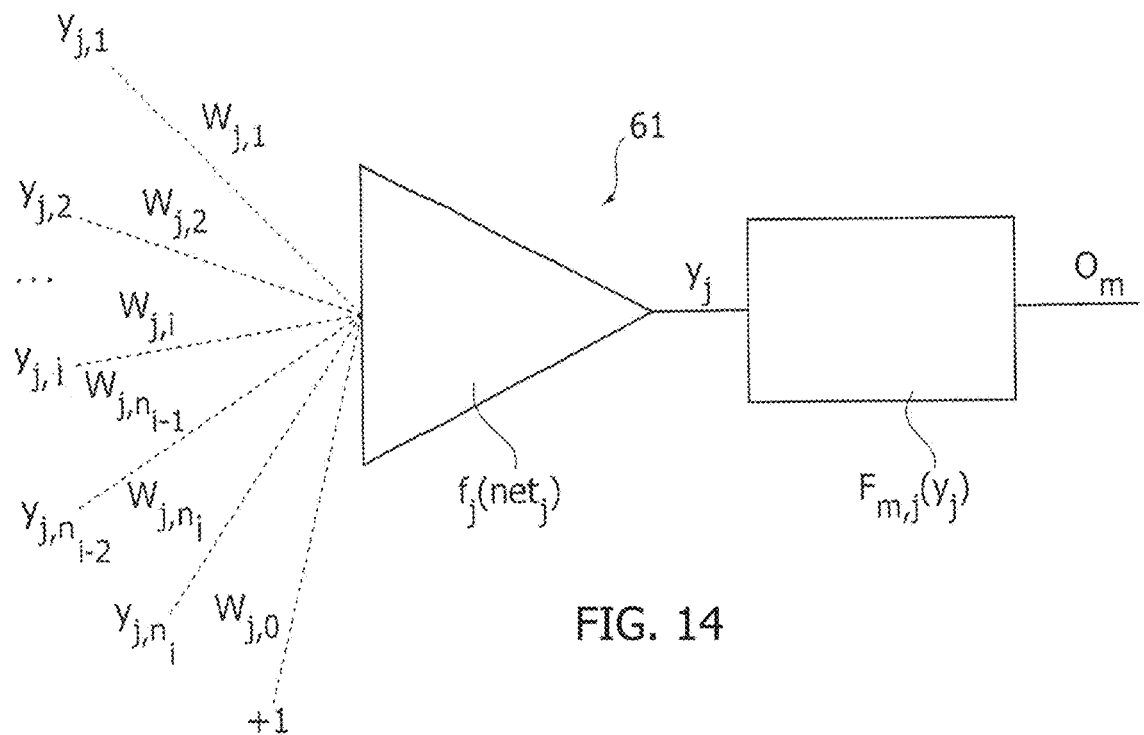

In one or more embodiments, EEG signal reconstruction to provide the two signals e_rec_drowsy and e_rec_wakeful may be performed as exemplified in FIGS. 13 and 14.

FIG. 13 and FIG. 14 are examples of diagrams of a possible network topology of an artificial neural network processing (as exemplified by stage 424 in FIG. 12) configured to correlate the PPG signal with EEG measurements available for training the first (and second) artificial neural network (ANN) stage 424, resulting in EEG signals e_rec (this designation will be used indifferently for e_rec_drowsy and e_rec_wakeful) reconstructed starting from the PPG signal S.

Training values, e.g., e_real (this designation will again be used indifferently for e_real_drowsy and e_real_wakeful) may include sets of EEG measurements performed on a wide sample of subjects (e.g. by conventional means such as a plurality of electrodes on the head surface) concurrently with detecting a PPG signal S.

Figure 12:
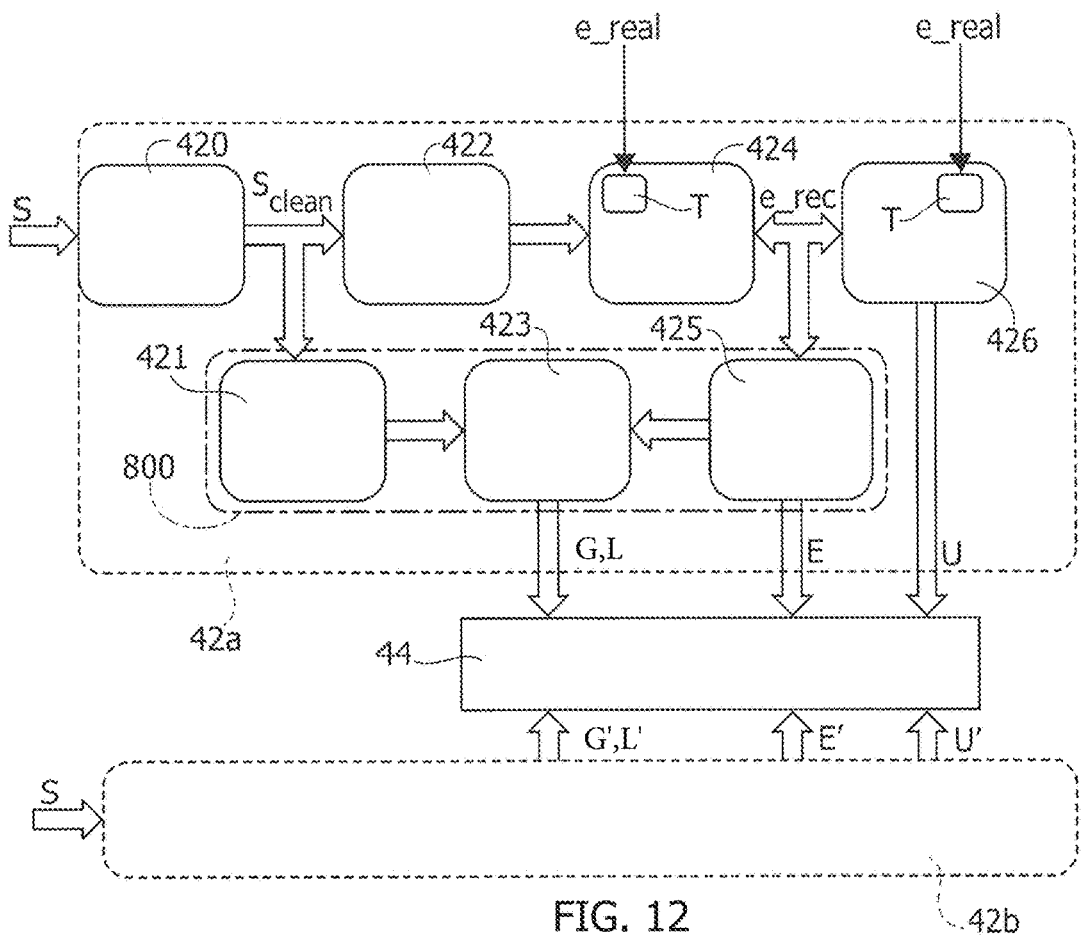
FIG. 12 is a block diagram exemplary of a possible arrangement a portion of the pipeline of FIG. 11.

These values can be used for training both neural networks circuits (e.g. Levenberg-Marquardt) of FIG. 12. The Levenberg-Marquardt multi-layer perceptron neural network, briefly LM-MLP NN, is found to be an adequate tool for use in learning a correlation between PPG signals and EEG samples/waveforms.

The (first) ANN stage 424 will thus facilitate reconstructing EEG signals e_rec of a subject both for drowsy (e_rec_drowsy) and wakeful (e_rec_wakeful) values, e.g. based on a Levenberg-Marquardt neural network multi-layer perceptron (briefly, LM MLP NN).

FIG. 13 is a diagram of a multi-layer perceptron, briefly MLP, with one input layer 601, a hidden layer 602 and an output layer 603, having a number of parallel perceptrons n1, n2, . . . , nO, for each respective layer.

The perceptrons in the layers are coupled to the input node of each neuron of the downstream layer (which may be referred to as a "fully connected feed forward" topology) and to a bias input node. For instance, the input layer 601 may receive an input array of values, e.g. I1, . . . , Ini, and a bias input, e.g. +1.

FIG. 14 is exemplary of the topological diagram of a single perceptron, e.g. a perceptron 61 belonging to the input layer 601.

The output layer 603 of the MLP may provide at output an array of output values O1, . . . , Om, . . . , Ono whose value may be described by the following equation:

$$O_m = G_{m,3}\left(\sum_{k=o}^{N} w_k \left(G_{m,2}\left(\sum_{i=o}^{N} w_{j,i}\left(G_{m,1}\left(\sum_{p=1}^{ni} k_p, I_p\right)\right)\right)\right)\right)$$

for $m = 1, \ldots, no$

The learning phase, e.g. to define the values of the weights associated to the output layer, may facilitate the minimization of an error function defined as:

$$e = \frac{1}{N}\sum_{j=1}^{N}(e\_rec_j - e\_real_j)^2$$

The Levenberg-Marquardt error-correction learning is expressed in the equation below:

$$w_{k+1} = w_k - (J_k^T J_k - \mu I)^{-1} J_k e_k$$

where the weight vector w is iteratively updated by the error vector e modified by the Jacobian matrix J and the scalar m.

For a LM-MLP NN (Levenberg-Marquardt Multi-Layer Perceptron Neural Network), the input bias array (e.g., +1) are given the values of the error vector e, and the output bias array (e.g., +1) are set to (1−e), thus ensuring the outliers in the inputs are scaled down in importance in the output layer.

The first artificial neural network circuit 424 may facilitate to complete such a reconstruction of the EEG signals both for drowsy and wakeful driver training sets.

In one or more embodiments, a mathematical analysis stage 800 (visible in FIG. 12 and further detailed in FIG. 15) may be configured to process the filtered "clean" PPG signal Sclean and the reconstructed EEG signal e_rec_drowsy to provide a set of vectors, e.g., [G, L, E], to the decision stage 44.

It will again be recalled that, while provided for brevity primarily in respect of the stage 42a, the same description herein applies, mutatis mutandis, also to the stage 42b. Consequently, in one or more embodiments, the stage 42b may include a respective mathematical analysis stage 800 configured to process the filtered "clean" PPG signal Sclean and the reconstructed EEG signal e_rec_wakeful to provide a respective set of vectors, e.g., [G', L', E'], to the decision stage 44.

For instance, the mathematical analysis stage 800 (both in 42a and in 42b) may include at least one processor block (e.g. a DSP or similar processor circuit) configured, in a manner known to those of skill in the art (e.g. via software) to perform mathematical analysis of the "clean" PPG signal Sclean from the PPG probe PD (e.g. as received—in digital form—from the input) to extract therefrom certain features to support further processing in the artificial neural network (ANN) stages downstream.

In one or more embodiments, calculating the values of the (first) set of vectors [G, L, E] may take place as exemplified in FIG. 15, which also applies to calculating the values of the (second) set of vectors [G', L', E'].

In one or more embodiments, the mathematical analysis stage 800 may include a first analysis stage 421, a second analysis stage 425, a feature extraction stage 423 and an optional combination stage 427.

In one or more embodiments, the first analysis stage 421 may receive the filtered "clean" PPG signal Sclean from the first filtering stage 420 and provide a first analysis vector L including a plurality of values, e.g., characteristics of the filtered "clean" PPG signals Sclean, e.g. L=[Ldia, Lsys, LpeakToPeak].

For instance, as discussed above in greater detail, the characteristics may include: the length of sub-curve of PPG waveform, for the diastolic phase Ldia; the length of sub-curve of PPG waveform, for the systolic phase, Lsys; and the length of sub-curve of PPG waveform between two consecutive SP peaks, LpeakToPeak. The suffixes sys and dia respectively denote the systolic and diastolic phases of the PPG signal which may be identified, with reference to the diagram of FIG. 1, as the portions O-SP (systolic) and DN-DP (diastolic), while the suffix peakToPeak denotes the phase between two consecutive SP peaks.

Similarly, the second analysis stage 425 may receive the reconstructed EEG signals e_rec (again this may apply to e_rec_drowsy in 42a and to e_rec_wakeful in 42b) from the first ANN circuit 424 and provide a second analysis vector E including a plurality of values, e.g., statistical characteristics of the reconstructed EEG signals e_rec, e.g. E=[μ(e_rec), G(e_rec), μ(R(e_rec))]. For instance, the statistical characteristics may include: a mean value of the reconstructed EEG signal, μ(e_rec); a standard deviation of the reconstructed EEG signal, G(e_rec), and a mean value of the autocorrelation function of the reconstructed EEG signal, μ(R(e_rec)).

Next, the feature extraction stage 423 may be configured to receive as input the first analysis vector L (respectively, L') and the second analysis vector E (respectively, E') and to provide as output a feature vector G (respectively, G'), containing a certain number of mathematical features G1 to G6, e.g. G=[G1, G2, G3, G4, G5, G6], resulting from processing input received.

In one or more embodiments, features G1 to G6 may be expressed by the following equations:

$$G_1 = \ln\left(\frac{1}{2}\left(\sum_{i=1}^{2} L_{sys}^i\right)\right)$$

$$G_2 = \ln\left(\frac{1}{2}\left(\sum_{i=1}^{2} L_{dia}^i\right)\right)$$

$$G_3 = \ln(L_{peakToPeak})$$

$$G_4 = ac(e\_rec) =$$

$$\left(\frac{1}{\sigma(e\_rec)^2}\right)\frac{1}{N}\left(\sum_{i=1}^{N \cdot k}((e\_rec(i) - \mu(e\_rec))(e\_rec(i+k) - \mu(e\_rec))\right)$$

$$G_5 = \sigma(e\_rec)$$

$$G_6 = \mu(e\_rec) = \frac{1}{N}\left(\sum_{i=1}^{N} e\_rec(i)\right)$$

Essentially, mathematical features G1 to G3 provide an indication of the "length" of the signal curve or path of the PPG signal in the systolic, diastolic phases (that is, so to say, "how long" each these signals remains in each phase) and of the peak-to-peak "length", while features G4 to G6 provide an indication of the statistical features of the reconstructed EEG signal e_rec.

In one or more embodiments, optionally, the first analysis vector L (respectively, L') and the feature vector G (respectively, G') may be combined in a combination stage 427, e.g. may be concatenated.

As a result, in one or more embodiments: the first set of vectors [G, L, E] calculated in the mathematical analysis stage 800 in the sub-stage 42a will depend on the sample data set e_real_drowsy; and the second set of vectors [G', L', E'] calculated in the mathematical analysis stage 800 in the sub-stage 42b will depend on the sample data set e_real_wakeful.

In one or more embodiments, the second artificial Neural Network (ANN) circuit 426 may receive the reconstructed EEG signal e_rec (e_rec_drowsy in 42a and e_rec_wakeful in 42b) from the first ANN circuit 424 and may be configured to process the reconstructed EEG signal e_rec via an artificial neural network, e.g., such as a multi-layer motor map neural network.

In one or more embodiments, the artificial neural network of the second ANN circuit 426 may be trained to provide a vector of selected weights U (for 42a) and U' (for 42b), including a plurality of selected weights, e.g., U=[u1, . . . , u6]; U'=[u1', . . . , u6'] to the decision stage 44, as discussed in the following in relation to FIG. 16.

In one or more embodiments, the second ANN circuit 426 may include a storage area T for a collection of EEG waveforms e_real (e_rec_drowsy in 42a and e_rec_wakeful in 42b), similarly to what described for the first ANN circuit 424. For instance: the second ANN circuit 426 in 42a may store a collection of EEG waveforms of drivers in a drowsy state e_real_drowsy; and the second ANN circuit 426 in 42b may store a collection of EEG waveforms of drivers in a wakeful state e_real_wakeful.

The reconstructed EEG signal e_rec (e_rec_drowsy in 42a and e_rec_wakeful in 42b) may thus be calculated as a function of either one of alternative driver states depending on which collection of EEG waveforms between e_real_drowsy and e_real_wakeful is stored in the respective memories T of the ANN circuits 424, 426, resulting in either a reconstructed drowsy EEG signal e_rec_drowsy or a reconstructed wakeful EEG signal e_rec_wakeful.

In one or more embodiments, the first vector of selected weights U in the sub-stage 42a, e.g. U=[u1, ..., u6], may facilitate calculating a level of attention DLA for a drowsy driver, while the second vector of selected weights U' in the sub-stage 42b, e.g. U'=[u1', ..., u6'], may facilitate calculating a level of attention DLA' for a wakeful driver.

In one or more embodiments, the first and second vectors of selected weights U, U' may be calculated with a similar procedure, as discussed in the following.

Figure 16:
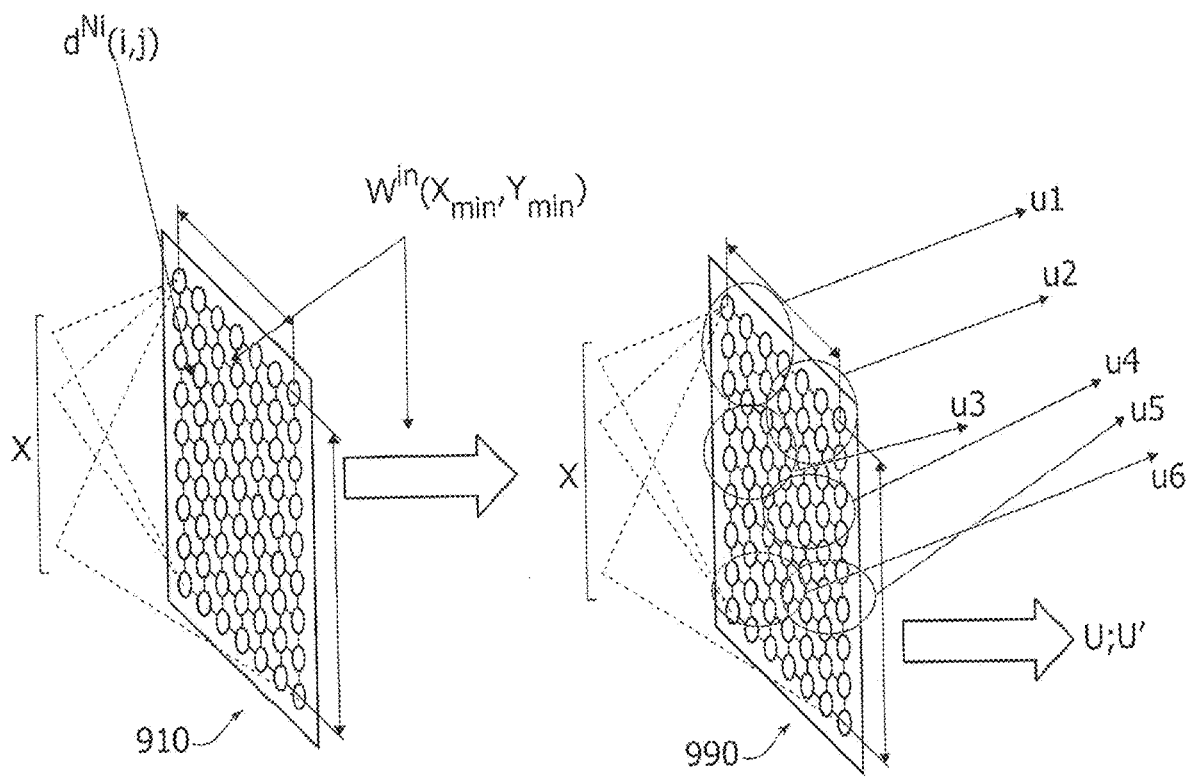
FIG. 16 is exemplary of possible artificial neural network signal processing in embodiments.

In one or more embodiments, the second ANN circuit 426 (both in 42a and in 42b) may implement a motor map neural system, as exemplified in FIG. 16. In one or more embodiments, a winner-take-all algorithm, e.g. SOMs, may be suited to perform the training of the neural network of the second ANN circuit 426. An extended SOM (Self Organizing Map) as schematically exemplified in FIG. 16 (where only the input layer IL and the output layer OL are visible) is found to be suited for use in one or more embodiments.

For instance, in one or more embodiments, the second ANN circuit 426 may include an input neural layer (e.g. lattice-like, for instance n*n=$n^2$ neuronal nodes) 900, which may receive as input the reconstructed EEG signals e_rec, and a corresponding output layer 990 (e.g. lattice-like, for instance n*n=$n^2$ neuronal nodes), which may provide at output the vector of selected weights U.

In one or more embodiments, the input layer 910 may include weights win(x, y, t) while the output layer may include weights u(x, y, t). In one or more embodiments, a random element μ(t) may be included with a view to improving the learning process.

In fact, from an initial distribution of random weights, and over many iterations, the SOM may be trained to facilitate providing at output a feature map of the input. The feature map may be provided at output in the form of a vector of selected weights U including a plurality of weight values, e.g. six values. The plurality of values may be the result of the selection at the output layer 990 of the neural network of a plurality of parameters of best matching units (BMUs) neurons. The BMU neurons may be those neurons that minimize a distance (based on certain metrics, e.g. Euclidean) between the synaptic weights (e.g., win) and the EEG samples, as discussed in the following.

In order to do so, the artificial neural network may be trained, e.g. its weights win(x,y,t), u(x,y,t) may be determined, through an iterative process based on providing "real" EEG datasets e_real to the neural network circuit. For instance, determining the BMU may involve iterating through all the (neuronal) nodes and calculating the Euclidean distance dNi(i,j) between a weight vector of each node and a current input vector; the node with a weight vector win(x,y,t) closest to the input vector e_rec may be tagged as the BMU.

The Euclidean distance may be given as:

$$d^{Ni}(i,j) = \sqrt{\sum_{i=1}^{N}(EEG_{rec}(i) - w^{Ni}(i))^2}$$

Nodes within the neighborhood of BMU nodes (including the BMU nodes) may have their weight vector adjusted according to the following equation:

$$w^{Ni}(t+1) = w^{Ni}(t) + \alpha \cdot \beta(x,y,t) \cdot (e\_rec - w^{Ni}(t))$$

where: t is the time-step; α is the learning rate; and β(x,y,t) is a parameter of the amount of influence a node's distance from the BMU has on its learning, e.g. a classical Gaussian function.

Essentially, the new adjusted weight $w^{Ni}(t+1)$ for a node of the neural network may be equal to the old weight $w^{Ni}(t)$, plus a fraction of the difference between the old weight $w^{Ni}(t)$ and the input vector e_rec.

Each of the components, e.g., u1, ..., ui, ..., u6, of the vector of selected weights U may vary in time according to the following equation: $u_i(t+1)=u_i(t)+\alpha\cdot\beta(x,y,t)\cdot$rand. A similar notation may apply to the vector of selected weights U'.

Consequently, the second ANN circuits 426 in the sub-stage 42a and the second ANN circuits 426 in the sub-stage 42b may provide respective vectors of selected weights U and U', each of the vectors including six values, e.g., U=[u1, ..., u6], U'=[u1', ..., u6'] indicative of parameters/weights of the output layer of the Self-Organizing Map (SOM) neural network.

Figure 17:
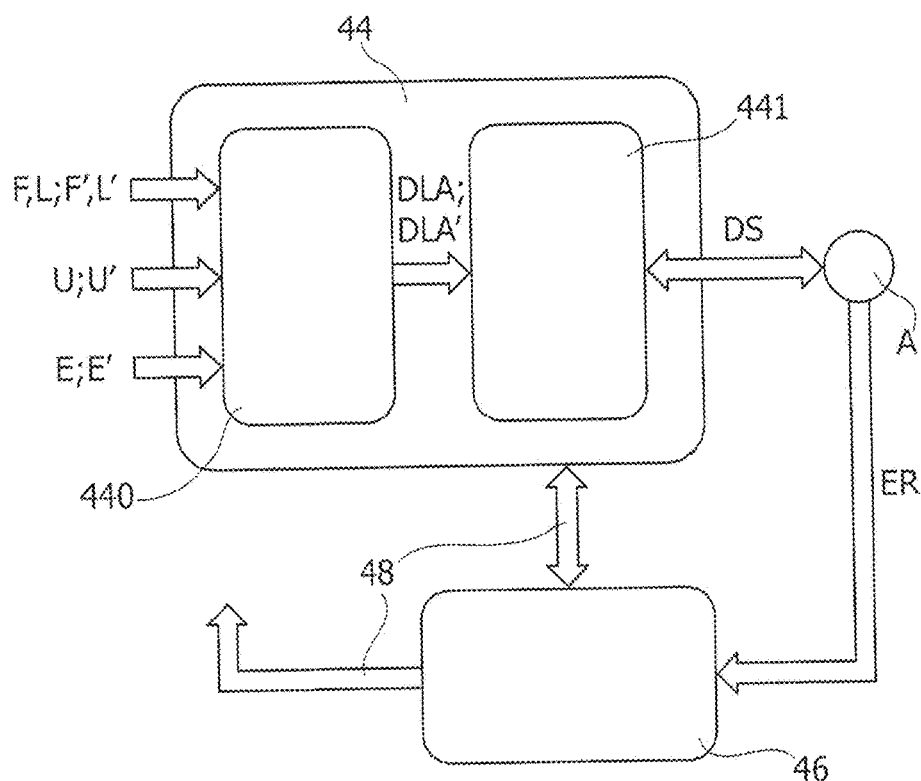
FIG. 17 is a functional diagram exemplary of possible signal processing in embodiments.

FIG. 17 is a flow chart exemplary of a possible mode of operation of the decision stage 44. In one or more embodiments, the decision stage 44, coupled to processing stage 42, may receive a "union" data set P (see FIGS. 11 and 12) including the first set of vectors [G, U, E, L] from the sub-processing stage 42a and the second set of vectors [G', U', E', L'] from the sub-processing stage 42b. In one or more embodiments, the decision stage 44 may be configured to process the sets of data from the processing stage 42 via neural network processing.

The Levenberg-Marquardt multi-layer perceptron neural network, briefly LM-MLP NN, is again found to provide an adequate tool for that purpose. In one or more embodiments as exemplified in FIG. 17, a selective output layer 440 may use a "defuzzification" function, e.g. a Takagi-Sugeno centroid calculated as a weighted sum, providing an array DLA(rec) of "reconstructed" driver level of attention values DLAn1, ..., DLAk, ..., DLAno whose values may be calculated according to the following equation:

$$DLA_k(rec) = \left(\frac{1}{6}\right)\left(\frac{\sum_{i=1}^{6} u_i^k G_i^k}{\sum_{i=1}^{6} u_i^k}\right)$$

where the index k refers to the kth member of the array and remaining symbols in the equations are the same as already defined in the foregoing.

For instance, the components of the vector of selected weights U may be regarded as the membership functions (e.g. weights of a weighted sum) of the feature vector G components G1, ..., G6, e.g. according to a Takagi-Sugeno-type de-fuzzification function, for instance as disclosed in T. Takagi and M. Sugeno: "Fuzzy Identification of Systems and Its Applications to Modeling and Control," IEEE Transactions on Systems, Man and Cybernetics, vol. SMC-15, no. 1, pp. 116-132, 1985. For instance, the first vector of selected weights U may be indicative of a first membership function to apply to mathematical features vector G of the reconstructed drowsy EEG signal e_rec_drowsy. Similarly, the second vector of selected weights U' may be indicative of a second membership function to apply to mathematical features vector G' of the reconstructed drowsy EEG signal e_rec_wakeful.

At each reconstructed driver level of attention value DLAk(rec) calculated from data based on the reconstructed EEG signals e_rec (that is e_rec_drowsy and e_rec_wakeful), a corresponding driver level of attention value DLAk (real) may be calculated according to the formula above, this time based on the sample EEG signals e_real.

Subsequently, computed reconstructed driver level of attention values DLA(rec) may be compared with the corresponding real driver level of attention values DLA(real) by computing an error metrics, for instance square or quadratic distance:

$$E = \left(\frac{1}{N}\right)\sum_{i=1}^{n}\left(\frac{1}{2}\right)(DLA_i(e\_real) - DLA_i(e\_rec))^2$$

where N denotes the number of reconstructed EEG signals used in the training set and the index i identifies each individual EEG samples.

It will be appreciated that an error E found to be smaller than the previously calculated error may indicate that the system is learning "well" insofar as it is minimizing with a quadratic dynamics the average error between the reconstructed driver level of attention values DLAk(rec) and the corresponding "real" ones DLAk(real).

The learning procedure as described can be continued until a desired accuracy is achieved or for a fixed amount of time, e.g. 3 epochs. The neural nodes of the LM-MLP NN441 may have a transfer function, e.g. a step function, to provide as an output a (classification) indicator DS, which, for instance, may facilitate evaluating whether the previously calculated level(s) of driver attention (or a combination thereof) is below or above a threshold value T, e.g. T=0.5.

The artificial neural network processing in the decision stage 44 may provide the indicator DS to user circuits A and error monitoring stage 46. In one or more embodiments, the indicator DS may have values ranging in a unitary interval, e.g. DS $\in$[0,1].

The indicator DS may be indicative of the level of attention of the driver as calculated by the neural network circuits 440, 441 of the decision stage 44. For instance, when the indicator DS has values within a first interval, e.g. 0<DS≤0.5, this may be indicative of a "drowsy" driver state, while a value of the indicator DS outside the interval, e.g. DS>0.5, may be indicative of a "wakeful" driver state.

The decision stage 44 will thus facilitate evaluating the level of attention of a subject, in a range of states, e.g. from drowsy state to wakeful state.

The indicator DS may be provided to further processing units and may be used to trigger an alert on an interface (see e.g. interface A in FIG. 11) such as a display, e.g. on the dashboard of the vehicle V.

The indicator DS may be provided to the error monitoring stage 46, which may trigger the activation of the feedback loop path 48 towards the decision stage 44 and/or the processing stage 42 to restart the learning phase of the neural networks respective circuits 426, 429, 44. For instance, neural network circuits may be re-trained to take into account changes in the dynamics of the PPG signals S, Sclean received.

The feedback loop path 48 may be operated to be activated: periodically, according to a planned safety-check schedule embedded in the error monitoring stage 46, e.g. once a month; due to a significant deviation (above a certain tolerance threshold) of the measured PPG signals S acquired from sensor(s) DP from the PPG signals used for the neural network training phase, e.g. due to a change in the driver; and/or due to the wear of/as a consequence of safety-checks performed on the electronic circuits.

The error monitoring stage 46 may trigger the activation of the branches of the feedback loop path 48 in a certain sequence. For instance, the sequence may include: trigger the start of a training phase for the decision stage 44, e.g. re-training the neural network; wait (e.g., for its convergence) for a desired time interval, e.g. a fixed number of epochs; and if the training phase does not converge within the desired time interval, trigger the start of a training phase for the processing stage 42, in particular for the second ANN circuit 426.

In one or more embodiments, optionally, it may be possible to iterate the procedure until the training phase for the decision stage 44 converges within the desired time interval.

In one or more embodiments, a method may include:
i) receiving (see e.g. 12, 14) PhotoPlethysmoGraphy, briefly PPG, signals (e.g. PPG) including systolic, diastolic and dicrotic phases (see e.g. SP, DP and DN in FIG. 1.)
ii) processing (e.g. at 14) the PPG signals, wherein the processing includes calculating the first ($\partial PPG/\partial t$) and second ($\partial 2PPG/\partial t2$) derivatives (time derivatives) of the PPG signals (PPG) and calculating:
a first set of values (e.g. "features" such as e.g. F1 to F18) indicative of the lengths of the signal paths of the PPG signal, the first derivative and the second derivative thereof in the systolic, diastolic and dicrotic phases (this first set of values facilitates characterizing the time lengths or durations of the various phases of the cardiac cycle, with the derivatives contributing information on the respective dynamics of systolic, diastolic and dicrotic);
a second set of values (e.g. F19 to F36) indicative of the relative durations of the PPG signal and the first and second derivatives thereof in the systolic, diastolic and dicrotic phases (this second set of values facilitates characterizing the ratios between the various phases, that is the "weight" of one phase with respect to the others, with the derivatives again contributing information on the ratios between the dynamics of the various phases),
a third set of values (e.g. F37 to F42) indicative of the time separation of peaks and/or valleys (see e.g. FIG. 8 in subsequent waveforms of the PPG signal (this third set of values facilitates characterizing the timing between subsequent cardiac cycles and between subsequent phases),
iii) applying artificial neural network processing (e.g. 16, 18) to the first, second and third set of values, wherein the artificial neural network processing includes artificial neural network training as a function of blood pressure signals to produce reconstructed blood pressure signals (e.g. SBPrec, DBPrec) reconstructed from the PPG signals.

In one or more embodiments, the artificial neural network processing may include (e.g. at 16) Polak-Ribiere neural network multi-layer perceptron processing to reconstruct a nonlinear component of the reconstructed blood pressure signals reconstructed from the PPG signals.

In one or more embodiments, the artificial neural network processing may include (e.g. at 18) self-organizing map, briefly SOM, processing to reconstruct a linear component of the reconstructed blood pressure signals reconstructed from the PPG signals.

One or more embodiments may include producing the reconstructed blood pressure signals by combining, optionally by adding, a nonlinear component and a linear component of the reconstructed blood pressure signals reconstructed from the PPG signals.

In one or more embodiments calculating the first set of values may include calculating values (e.g. F4 to F6, F10 to F12, F16 to F18) indicative of standard deviations of the lengths of the signal paths of the PPG signal, the first derivative and the second derivative thereof in the systolic, diastolic and dicrotic phases.

One or more embodiments may include calculating the lengths of the signal paths of the first derivative and the second derivative of the PPG signal by means of the Simpson rule.

In one or more embodiments, the artificial neural network processing may include artificial neural network training as a function of systolic and diastolic blood pressure signals to produce reconstructed systolic blood pressure signals (e.g. SBPrec) and diastolic blood pressure signals (e.g. DBPrec) reconstructed from the PPG signals.

One or more embodiments may include:
collecting PPG signals from at least one PPG sensor (e.g. S),
applying (12) to the PPG signals collected from at least one PPG sensor at least one of filtering, optionally band-pass filtering, and/or PPG signal pattern recognition (e.g. as disclosed in Italian Patent Application No. 102017000081018 and the various Rundo et al. papers cited in the foregoing),
receiving (e.g. at 14) the PPG signals after the at least one of filtering and/or PPG signal pattern recognition.

A system according to one or more embodiments may include:
i) an input circuit block configured to receive PPG signals including systolic, diastolic and dicrotic phases,
ii) a processing circuit block active on the PPG signals, wherein the processing circuit block (14) includes a calculator configured to calculate the first and second derivatives of the PPG signals as well as:
a first set of values indicative of the lengths of the signal paths of the PPG signal, the first derivative and the second derivative thereof in the systolic, diastolic and dicrotic phases,
a second set of values indicative of the relative durations of the PPG signal and the first and second derivatives thereof in the systolic, diastolic and dicrotic phases,
a third set of values indicative of the time separation of peaks and/or valleys in subsequent waveforms of the PPG signal,
iii) an artificial neural network circuit configured to process the first, second and third set of values, wherein the artificial neural network circuit is configured to perform artificial neural network training as a function of blood pressure signals to produce reconstructed blood pressure signals reconstructed from the PPG signals,
the system configured to operate with the method according to one or more embodiments.

In one or more embodiments such a system may include:
at least one PPG signal probe (e.g. S) to provide the PPG signals including systolic, diastolic and dicrotic phases, and/or
a presentation unit (e.g. D) to present the reconstructed blood pressure signals reconstructed from the PPG signals.

One or more embodiments may include a computer program product loadable in the memory of at least one processing circuit (e.g. 14, 16, 18) and including software code portions for executing the steps of the method of one or more embodiments when the product is run on at least one processing circuit.

In one or more embodiments, a method of processing electrophysiological signals may include:
collecting a PhotoPlethysmoGraphy, briefly PPG, signal (for instance, S) via a PPG sensor (for instance, PD);
processing (for instance, blocks 42, 44; 42a, 42b) the PPG signal, wherein processing may include generating via artificial neural network processing (for instance, blocks 424, 426, 44) of the PPG signal a reconstructed EEG signal (for instance, e_rec), the artificial neural network processing of the PPG signal including training at least one artificial neural network circuit over a training set of signals (for instance, e_real) produced during sampling a sample set of EEG signals; and
providing the reconstructed EEG signal to a user circuit (for instance, blocks 800, 44, A). In one or more embodiments, processing the PPG signal may include at least one of filtering (for instance, 420) and normalizing (for instance, 422) the PPG signal collected via a PPG sensor prior to artificial neural network processing (for instance, 424, 426) of the PPG signal.

One or more embodiments may include: sensing (for instance, blocks 46, A) a reconstruction error signal (for instance, ER) indicative of the accuracy of the reconstructed EEG signals; and activating (for instance, block 48), as a result of sensing the error signal, training of the at least one artificial neural network circuit (for instance, blocks 424, 426, 44) over a fresh training set (for instance, e_real) of signals produced during sampling a sample set of EEG signals.

It will be otherwise understood that the various individual implementing options exemplified throughout the figures accompanying this description are not necessarily intended to be adopted in the same combinations exemplified in the figures. One or more embodiments may thus adopt these (otherwise non-mandatory) options individually and/or in different combinations with respect to the combination exemplified in the accompanying figures.

One or more embodiments may include triggering training of the at least one artificial neural network circuit over a fresh training set as a result of reception of a re-training trigger signal from at least one of: an error monitoring stage (for instance, block 46); a periodic internal trigger generator; or an alert interface (for instance, block A).

In one or more embodiments, the artificial neural network processing of the PPG signal may include: first artificial neural network processing (for instance, 424) to map reconstructed EEG signals onto PPG signals; and second artificial neural network processing (for instance, 426) of the reconstructed EEG signals (e_rec) mapped onto PPG signals to produce a selected set (for instance, U, U') of output weights.

In one or more embodiments, the first artificial neural network processing (for instance, block 424) may include Levenberg-Marquardt multilayer perceptron processing. Additionally, or independent of the first artificial neural network processing, the second artificial neural network processing (for instance, 426) may include Self Organizing Map, briefly SOM, motor map processing.

One or more embodiments may include fuzzy inference processing, preferably via Takagi-Sugeno centroid fuzzy operator, the selected set of output weights.

One or more embodiments may include generating via artificial neural network processing of the PPG signal: a first reconstructed EEG signal (for instance, e_rec_drowsy) as a function of a first training set of signals (for instance, e_real_drowsy) produced during sampling a sample set of EEG signals in a first mental attention state; and a second reconstructed EEG signal (for instance, e_rec_wakeful) as a function of a second training set of signals (for instance, e_real_wakeful) produced during sampling a sample set of EEG signals a sample set of EEG signals in a second mental attention state.

One or more embodiments may include the steps of:
calculating (for instance, 440) from the first reconstructed EEG signal (for instance, e_rec_drowsy) a first reconstructed level of attention indicator (for instance, DLA);
calculating (for instance, 440) from the second reconstructed EEG signal (for instance, e_rec_wakeful) a second reconstructed level of attention indicator (for instance, DLA');
calculating (for instance, 440, 441) a resulting attention indicator (for instance, DS) as a combination of the first reconstructed level of attention indicator and the second reconstructed level of attention;
comparing (for instance, 441) the resulting attention indicator with a threshold value; and
producing an attention indicator signal (for instance, A) as a function of the result of the act of comparing.

One or more embodiments may include generating a reconstructed EEG signal via artificial neural network, briefly ANN, circuits (for instance, 424, 426, 44; 42, 42a, 42b) as a function of the PPG signals (for instance, S, Sclean) which may include training the artificial neural network circuits with datasets (for instance, e_real) of EEG signals stored in a memory space (for instance, T).

One or more embodiments may include: collecting the PPG signal from the driver (for instance, D) of a vehicle (for instance, V) via a PPG sensor on board the vehicle; and providing the reconstructed EEG signal to a user circuit (for instance, 800, 44, A) on board the vehicle, wherein the reconstructed EEG signal may be indicative of a level of attention of the driver (for instance, D).

A system (for instance, 40) according to one or more embodiments may include:
a PPG sensor (for instance, PD), configured to collect a PhotoPlethysmoGraphy, briefly PPG, signal; and
processing circuitry (for instance, 42, 44; 42a, 42b) coupled to the PPG sensor to receive the PPG signal therefrom, the processing circuitry including artificial neural network processing circuits (for instance, 424, 426, 44) and configured to provide a reconstructed EEG signal (for instance, e_rec) to a user circuit (for instance, 800, 44, A) according to embodiments.

One or more embodiments may include a vehicle (for instance, V) which may be equipped with a system (for instance, 40) according to embodiments in combination with at least one driver assistance device (for instance, A), the driver assistance device (A) configured to operate as a function of the reconstructed EEG signal (for instance, e_rec).

One or more embodiments may include a computer program product loadable in the memory of at least one processing circuit and including software code portions for executing the steps of the method according to embodiments when the product is run on at least one processing circuit.

Without prejudice to the underlying principles, the details and embodiments may vary, even significantly, with respect to what has been described by way of example only, without departing from the extent of protection.

What is claimed is:

1. A method of processing electrophysiological signals, the method comprising:
receiving a PhotoPlethysmoGraphy (PPG) signal from a user via a PPG sensor;
generating, by a processor and via artificial neural network processing of the PPG signal, a reconstructed ElectroEncephaloGram (EEG) signal, the artificial neural network processing of the PPG signal comprising training at least one artificial neural network circuit over a training set of signals produced during a sampling of a sample set of EEG signals; and
alerting the user, via an interface, of a level of attention of the user based on providing the reconstructed EEG signal, the level of attention of the user comprising an attention state from drowsy to wakeful.

2. The method of claim 1, further comprising at least one of filtering the PPG signal or normalizing the PPG signal prior to artificial neural network processing of the PPG signal.

3. The method of claim 1, further comprising:
sensing a reconstruction error signal indicative of an accuracy of the reconstructed EEG signal; and
activating, as a result of sensing the reconstruction error signal, training of the at least one artificial neural network circuit over a fresh training set of signals produced during the sampling of the sample set of EEG signals.

4. The method of claim 3, further comprising triggering training of the at least one artificial neural network circuit over the fresh training set in response to a reception of a re-training trigger signal from at least one of an error monitoring stage; a periodic internal trigger generator; or an alert interface.

5. The method of claim 1, wherein the artificial neural network processing of the PPG signal comprises:
a first artificial neural network processing to map reconstructed EEG signals onto the PPG signal; and
a second artificial neural network processing of the reconstructed EEG signals mapped onto the PPG signal to produce a selected set of output weights.

6. The method of claim 5, wherein the first artificial neural network processing comprises Levenberg-Marquardt multilayer perceptron processing.

7. The method of claim 5, wherein the second artificial neural network processing comprises a Self-Organizing Map motor map processing.

8. The method of claim 5, further comprising fuzzy inference processing of the selected set of output weights.

9. The method of claim 1, further comprising generating via artificial neural network processing of the PPG signal:
a first reconstructed EEG signal as a function of a first training set of signals produced during the sampling of the sample set of EEG signals in a first mental attention state; and
a second reconstructed EEG signal as a function of a second training set of signals produced during the sampling of the sample set of EEG signals in a second mental attention state.

10. The method of claim 9, further comprising:
- determining, from the first reconstructed EEG signal, a first reconstructed level of attention indicator;
- determining, from the second reconstructed EEG signal, a second reconstructed level of attention indicator;
- determining a resulting attention indicator as a combination of the first reconstructed level of attention indicator and the second reconstructed level of attention indicator;
- comparing the resulting attention indicator with a threshold value; and
- producing an attention indicator signal in response to comparing the resulting attention indicator with the threshold value.

11. The method of claim 1, wherein generating the reconstructed EEG signal via artificial neural network processing of the PPG signal comprises training the artificial neural network circuits with datasets of EEG signals stored in a memory space.

12. The method of claim 1, further comprising:
- collecting the PPG signal from a driver of a vehicle via the PPG sensor located on board the vehicle, wherein the driver of the vehicle is the user; and
- providing the reconstructed EEG signal to a user circuit on board the vehicle, wherein the reconstructed EEG signal is indicative of a level of attention of the driver, and wherein the user circuit is the interface.

13. A system, comprising:
- an interface;
- a PPG sensor configured to collect a PhotoPlethysmoGraphy (PPG) signal from a user; and
- processing circuitry coupled to the PPG sensor and configured to receive the PPG signal from the PPG sensor, the processing circuitry comprising artificial neural network processing circuits and configured to:
  - generate, via the artificial neural network processing circuits, a reconstructed ElectroEncephaloGram (EEG) signal from the PPG signal, the artificial neural network processing circuits being configured to train at least one artificial neural network circuit over a training set of signals produced during a sampling of a sample set of EEG signals; and
  - alerting the user, via the interface, of a level of attention of the user based on provide the reconstructed EEG signal, the level of attention of the user comprising an attention state from drowsy to wakeful.

14. The system of claim 13, wherein generating the reconstructed EEG signal from the PPG signal comprises:
- mapping reconstructed EEG signals onto the PPG signal; and
- mapping the reconstructed EEG signals onto the PPG signal to produce a selected set of output weights.

15. The system of claim 13, wherein the processing circuitry is configured to:
- sense a reconstruction error signal indicative of an accuracy of the reconstructed EEG signal; and
- activate, as a result of sensing the reconstruction error signal, training of the at least one artificial neural network circuit over a fresh training set of signals produced during the sampling of the sample set of EEG signals.

16. A vehicle, comprising:
- a driver assistance device comprising an interface;
- a PPG sensor configured to collect a PhotoPlethysmoGraphy (PPG) signal from a user; and
- processing circuitry coupled to the PPG sensor and configured to receive the PPG signal from the PPG sensor, the processing circuitry comprising artificial neural network processing circuits and configured to:
  - generate, via the artificial neural network processing circuits, a reconstructed ElectroEncephaloGram (EEG) signal from the PPG signal, the artificial neural network processing circuits being configured to train at least one artificial neural network circuit over a training set of signals produced during a sampling of a sample set of EEG signals; and
  - alerting the user, via the interface, of a level of attention of the user based on the reconstructed EEG signal, the level of attention of the user comprising an attention state from drowsy to wakeful.

17. The vehicle of claim 16, wherein the processing circuitry is configured to:
- sense a reconstruction error signal indicative of an accuracy of the reconstructed EEG signal; and
- activate, as a result of sensing the reconstruction error signal, training of the at least one artificial neural network circuit over a fresh training set of signals produced during the sampling of the sample set of EEG signals.

18. A computer program product loadable in a memory of a processing circuit and executable by the processing circuit, the computer program product comprising instructions for:
- receiving a PhotoPlethysmoGraphy (PPG) signal from a user via a PPG sensor;
- generating, by a processor and via artificial neural network processing of the PPG signal, a reconstructed ElectroEncephaloGram(EEG) signal, the artificial neural network processing of the PPG signal comprising training at least one artificial neural network circuit over a training set of signals produced during a sampling of a sample set of EEG signals; and
- alerting the user, via an interface, of a level of attention of the user based on the reconstructed EEG signal, the level of attention of the user comprising an attention state from drowsy to wakeful.

19. The computer program product of claim 18, wherein the artificial neural network processing of the PPG signal further comprises:
- sensing a reconstruction error signal indicative of an accuracy of the reconstructed EEG signal; and
- activating, as a result of sensing the reconstruction error signal, training of the at least one artificial neural network circuit over a fresh training set of signals produced during the sampling of the sample set of EEG signals.

20. The computer program product of claim 18, wherein generating the reconstructed EEG signal from the PPG signal comprises:
- mapping reconstructed EEG signals onto the PPG signal; and
- mapping the reconstructed EEG signals onto the PPG signal to produce a selected set of output weights.

* * * * *